United States Patent [19]

Matsuoka et al.

[10] Patent No.: US 6,559,149 B1
[45] Date of Patent: May 6, 2003

(54) METHOTREXATE DERIVATIVES

(75) Inventors: Hiroharu Matsuoka, Shizuoka (JP); Hiroshi Suzuki, Tokyo (JP); Nobuaki Kato, Shizuoka (JP); Keiichiro Tsuji, Shizuoka (JP); Toshio Kuroki, Shizuoka (JP); Noriaki Maruyama, Shizuoka (JP); Kazuya Nakagomi, Shizuoka (JP)

(73) Assignee: Chugai Seiyaku Kabushiki Kaisha, Tokyo (JP)

(*) Notice: Subject to any disclaimer, the term of this patent is extended or adjusted under 35 U.S.C. 154(b) by 0 days.

(21) Appl. No.: 08/256,441

(22) PCT Filed: Jan. 27, 1993

(86) PCT No.: PCT/JP93/00096

§ 371 (c)(1),
(2), (4) Date: Jul. 12, 1994

(87) PCT Pub. No.: WO93/15077

PCT Pub. Date: Aug. 5, 1993

(30) Foreign Application Priority Data

Jan. 27, 1992 (JP) .............................................. 4-053051
Feb. 13, 1992 (JP) .............................................. 4-075106
Mar. 16, 1992 (JP) .............................................. 4-108320
Mar. 24, 1992 (JP) .............................................. 4-115126

(51) Int. Cl.$^7$ .......................................... C07D 487/04
(52) U.S. Cl. ...................................... 514/249; 544/260
(58) Field of Search ................................ 514/258, 249; 544/260

(56) References Cited

U.S. PATENT DOCUMENTS 4,490,529 A    12/1984   Rosowsky ................... 544/260
5,354,753 A  * 10/1994   Ohi et al. ................... 514/258

FOREIGN PATENT DOCUMENTS

| EP | 0048000   |   | 3/1982  |
| JP | 5-132485  | * | 5/1993  |
| JP | 5-339268  | * | 12/1993 |
| JP | 6-16670   | * | 1/1994  |
| WO | 92-03436  | * | 3/1992  |
| WO | 93-15077  | * | 8/1993  |

OTHER PUBLICATIONS

Worth et al. Jour. Med. Chem vol. 21 pp331–7 (1978).*
Venditti et al. Cancer Research, vol. 20 No. 10 pp. 698–733, (1960).*
Broughton et al., Chemical Abstracts, vol. 115:247448, 1991.*
Chabner et al., *Polyglutamation of Methotrexate*, The Journal of Clinical Investigation, Inc., vol. 76, pp. 907–912, Sep. 1985.
Montgomery et al., *Analogues of Methotrexate*, Journal of Medicinal Chemistry, vol. 22, No. 7, pp. 862–868 Jan 15, 1979.

Rosowsky et al., *Methotrexate Analogues. 26. Inhibition of Dihydrofolate Reductase and Folylpolyglutamate Synthetase Activity and in Vitro Tumor Cell Growth by Methotrexate and Aminopterin Analogues Containing a Basic Amino Acid Side Chain*, Journal of the Medical Chemistry, vol. 29, pp. 655–660, 1986.

Rosowsky et al., *Methotrexate analogues. 19. Replacement of the Glutamate Side Chain in Classical Antifolates by L–Homocysteic Acid and L–Cysteic Acid: Effect on Enzyme Inhibition and Antitumor Activity*, Journal of the Medical Chemistry, vol. 27, pp. 600–604, 1984.

Rosowsky et al., *Methotrexate Analogues. 33. $N^\delta$–Acyl–$N^\alpha$–(4–amino–4–deoxypteroyl)–L–ornithine Derivatives: Synthesis and in Vitro Antitumor Activity*, Journal of the Medical Chemistry, vol. 31, pp. 1332–1337, 1988.

Rosowsky et al., *Methotrexate Analogues. 28. Synthesis and Biological Evaluation of New γ–Monoamides of Aminopterin and Methotrexate*, Journal of the Medical Chemistry, vol. 29, pp. 1703–1709, 1986.

Piper et al., *10–Propargylaminopterin and Alkyl Homologues of Methotrexates as Inhibitors of Folate Metabolism*, Journal of the Medical Chemistry, vol. 25, pp. 877–880, 1982.

Rosowsky et al., *Methotrexate Analogues. 20. Replacement of Glutamate by Longer–Chain Amino Diacids: Effects on Dihydrofolate Reductase Inhibition, Cytotoxicity, and Vivo Antitumor Activity*, Journal of the Medical Chemistry, vol. 26, pp. 1719–1724, 1983.

Piper et al., *Studies on Analogues of Classical Antifolates Bearing the Naphthoyl Group in Place of Benzoyl in the Side Chain*, Journal of the Medical Chemistry, vol. 36, pp. 4161–4171, 1993.

Galivan et al, *γ–Fluoromethotrexate: Synthesis and biological activity of a potent inhibitor of dihydrofolate reductase with greatly diminished ability to form poly–γ–glutamates*, Proc. Natl. Acad. Sci. USA, vol. 82, pp. 2598–2602, May 1985.

Degraw et al., *Synthesis and Antifolate Properties of 9–Alkyl–10–deazaminopterins*, Journal of the Medical Chemistry, vol. 33, pp. 212–215, 1990.

(List continued on next page.)

*Primary Examiner*—Richard L. Raymond

(57) ABSTRACT

Antirheumatic agent containing as an active ingredient a compound resented by the following general formula (II):

8 Claims, 3 Drawing Sheets

OTHER PUBLICATIONS

Abraham et al., *Folate Analogues. 33. Synthesis of Folate and Antifolate Poly–γ–glutamates by [(9–Fluorenylmethoxy)oxy]carbonyl Chemistry and Biological Evaluation of Certain Methotrexate Polyglutamate Polylysine Conjugates as Inhibitors of the Growth of H35 Hepatoma Cells*, Journal of Medical Chemistry, vol. 33, pp. 711–717, 1990.

Cosulich et al, *Analogs of Pteroylglutamic Acid. IX. Derivatives with Substituents on the Benzene Ring*, Journal of the American Chemical Society, vol. 75, No. 19, Oct. 5, 1953.

* cited by examiner

METHOTREXATE DERIVATIVES

This application is a 371 of PCT /JP93/00096, filed Jan. 27, 1993.

1. Technical Field

This invention relates to novel methotrexate derivatives, more particularly to novel methotrexate derivatives that are useful as antirheumatic agents.

2. Background Art

Methotrexate had long been used as a therapeutic agent for leukemia but ever since Gubner et al. reported its effectiveness in the treatment of rheumatoid arthritis (RA) and psoriasis in 1951, methotrexate has been used as a therapeutic agent for RA in both Europe and the United States of America. Fairly recently, detailed investigations were conducted on the method of administration and dose of methotrexate to reveal that low-dose methotrexate therapy causes fairly less side effects and yet exhibit excellent efficacy. However, the administration of methotrexate causes various side effects that cannot be ignored, such as hepatopathy and pulmonary fibrosis and, hence, a strong need exists for the advent of drugs that cause lesser side effects without compromise in their efficacy.

The present inventors conducted intensive studies in search for methotrexate derivatives that exceed methotrexate in efficacy as a rheumatism treating agent. The present invention has been accomplished on the basis of these studies.

DISCLOSURE OF THE INVENTION

The present invention provides methotrexate derivatives that are represented by the following general formula (II):

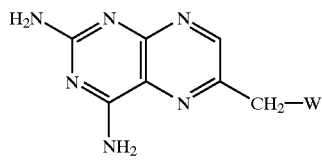

(II)

{where W is a group represented by the general formula:

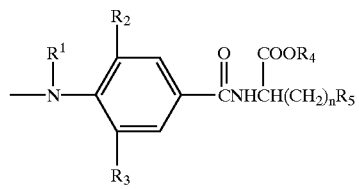

[where $R_1$ is a lower alkyl group having 1–4 carbon atoms; $R_2$ is a lower alkyl group having 1–4 carbon atoms or a trifluoromethyl group; $R_3$ is a hydrogen atom, a lower alkyl group having 1–4 carbon atoms or a trifluoromethyl group; $R_4$ is a hydrogen atom or a lower alkyl group having 1–4 carbon atoms; $R_5$ is a group represented by the general formula $COOR_6$ (where $R_6$ is a hydrogen atom or a lower alkyl group having 1–4 carbon atoms) or a group represented by the formula $SO_3H$; and n is an integer of 1–4], or the general formula:

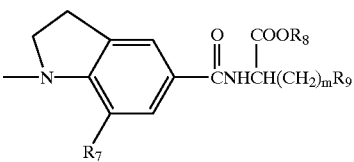

[where $R_7$ is a lower alkyl group having 1–4 carbon atoms; $R_8$ is a hydrogen atom or a lower alkyl group having 1–4 carbon atoms; $R_6$ is a group represented by the general formula $COOR_{10}$ (where $R_{10}$ is a hydrogen atom or a lower alkyl group having 1–4 carbon atoms) or a group represented by the formula $SO_3H$; and m is an integer of 1–4], or the general formula:

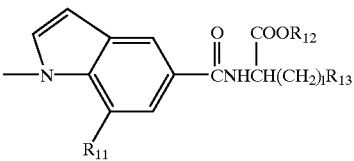

[where $R_{11}$ is a hydrogen atom or a lower alkyl group having 1–4 carbon atoms; $R_{12}$ is a hydrogen atom or a lower alkyl group having 1–4 carbon atoms; $R_{13}$ is a group represented by the general formula $COOR_{14}$ (where $R_{14}$ is a hydrogen atom or a lower alkyl group having 1–4 carbon atoms) or a group represented by the formula $SO_3H$; and l is an integer of 1–4], or the general formula:

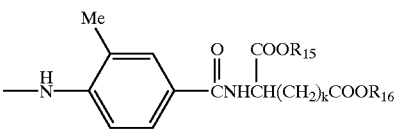

[where $R_{15}$ is a hydrogen atom or a lower alkyl group having 1–4 carbon atoms; $R_{16}$ is a hydrogen atom or a lower alkyl group having 1–4 carbon atoms; and k is an integer of 2 or 3].

The present invention also relates to the use of these compounds as antirheumatics. The antirheumatics of the present invention include a known compound, namely, 3'-methylaminopterin (see Cancer Research, Vol. 20, No. 10, 698–733, 1960); however, the use of this compound as an antirheumatic agent has not been known.

BEST MODE FOR CARRYING OUT THE INVENTION

Figure 1:
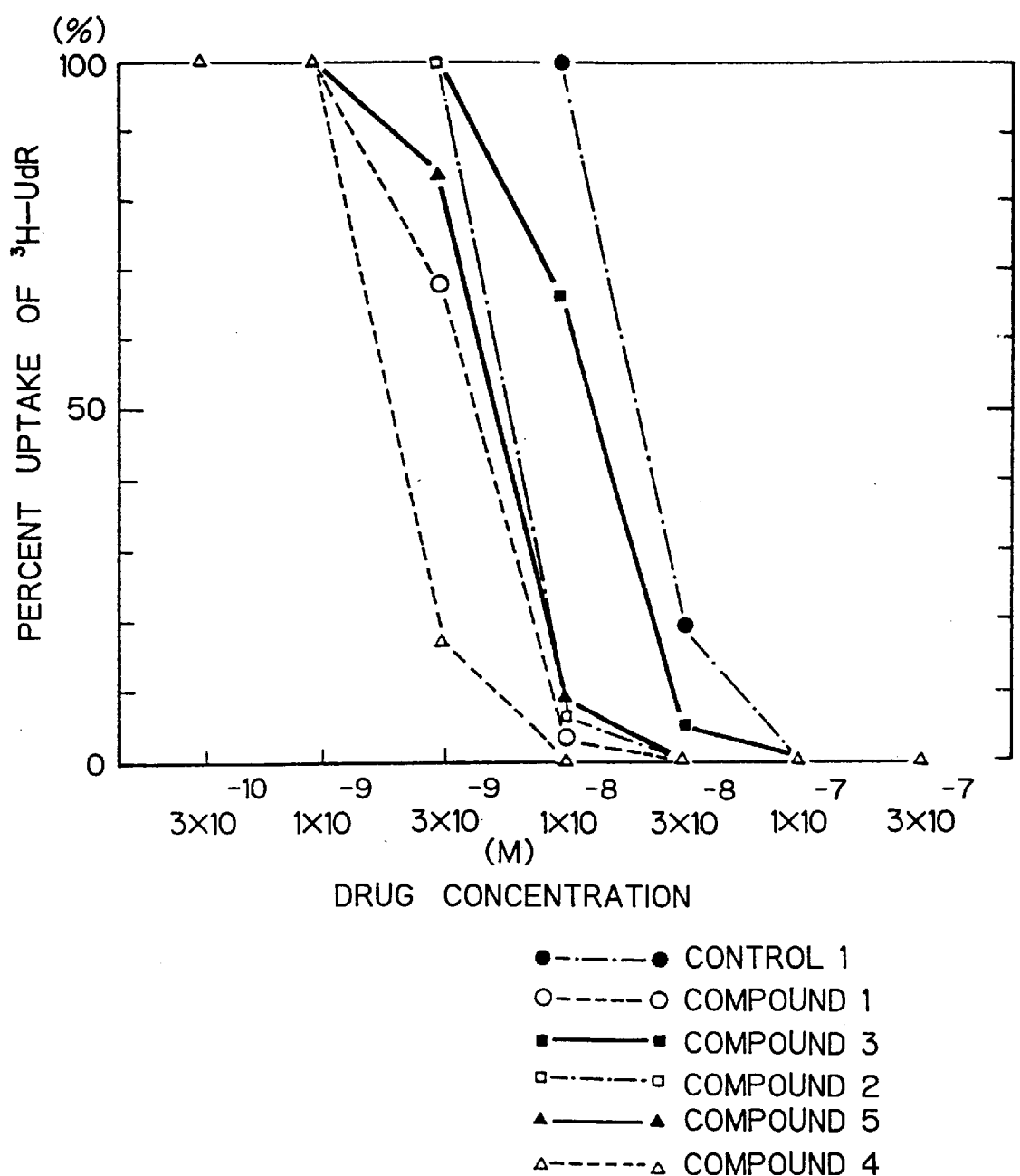
FIGS. 1, 2 and 3 show the amounts (ratio) of $^3$H-UdR to be uptake at a respective concentration of drugs to be tested.

The compounds of the present invention may typically be synthesized by the following methods. (Method A)

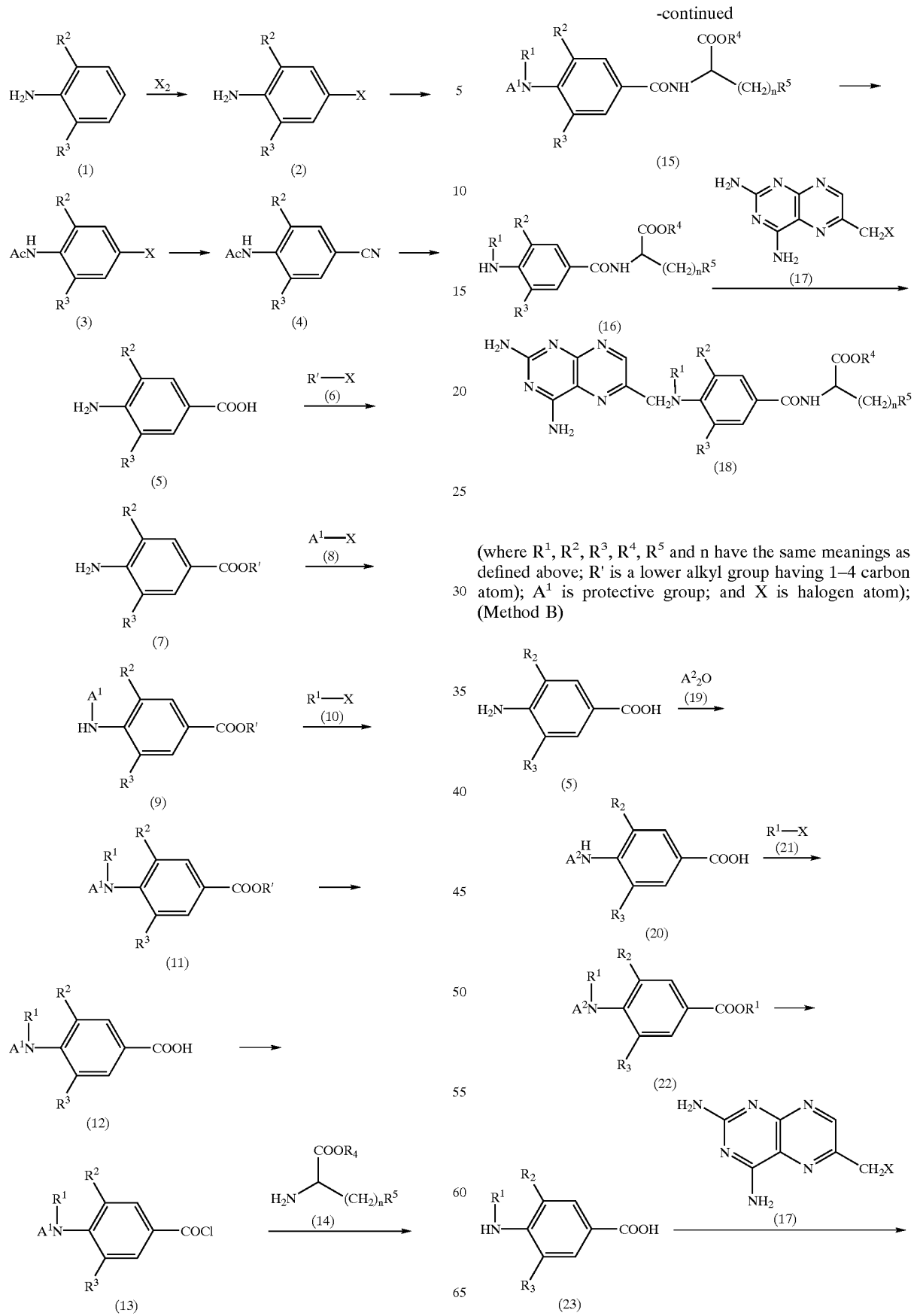
(where $R^1$, $R^2$, $R^3$, $R^4$, $R^5$ and n have the same meanings as defined above; R' is a lower alkyl group having 1–4 carbon atom); $A^1$ is protective group; and X is halogen atom); (Method B)

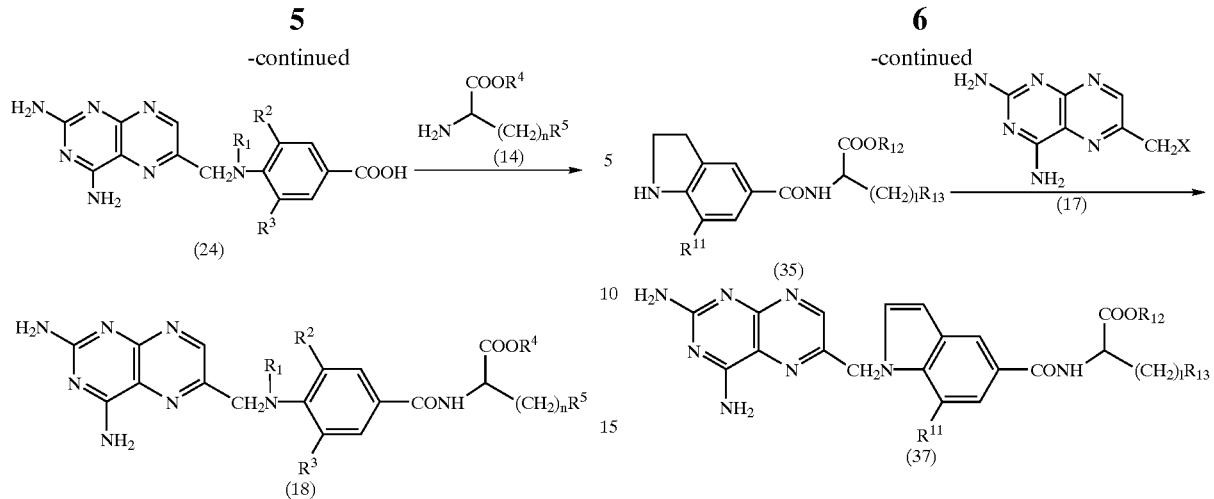

(where $R^1$, $R^2$, $R^3$, $R^4$, $R^5$ and n have the same meanings as defined above; $A^2$ is a protective group; and X is a halogen atom); (Method C)

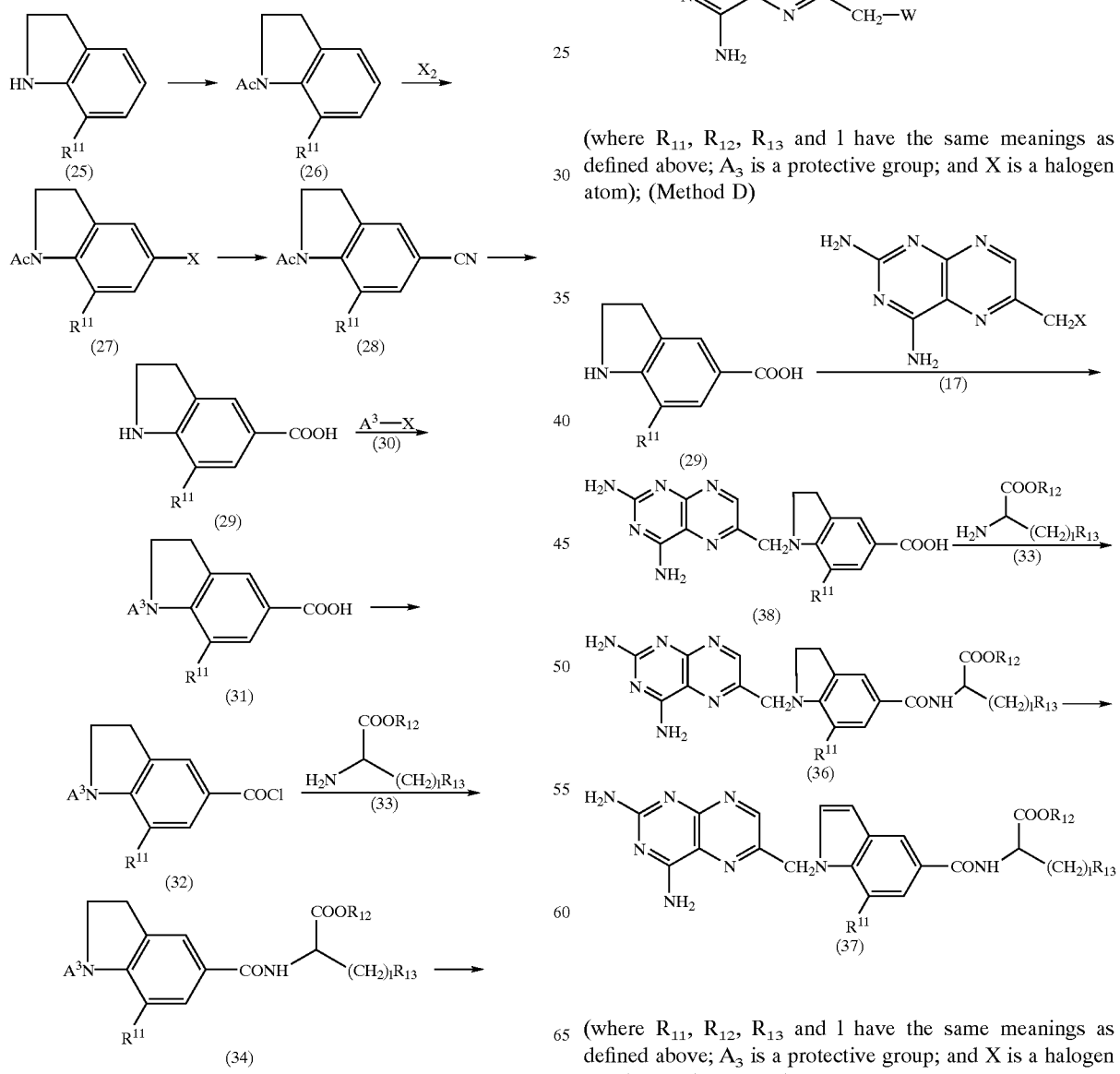

(where $R_{11}$, $R_{12}$, $R_{13}$ and l have the same meanings as defined above; $A_3$ is a protective group; and X is a halogen atom); (Method D)

(where $R_{11}$, $R_{12}$, $R_{13}$ and l have the same meanings as defined above; $A_3$ is a protective group; and X is a halogen atom); and (Method E)

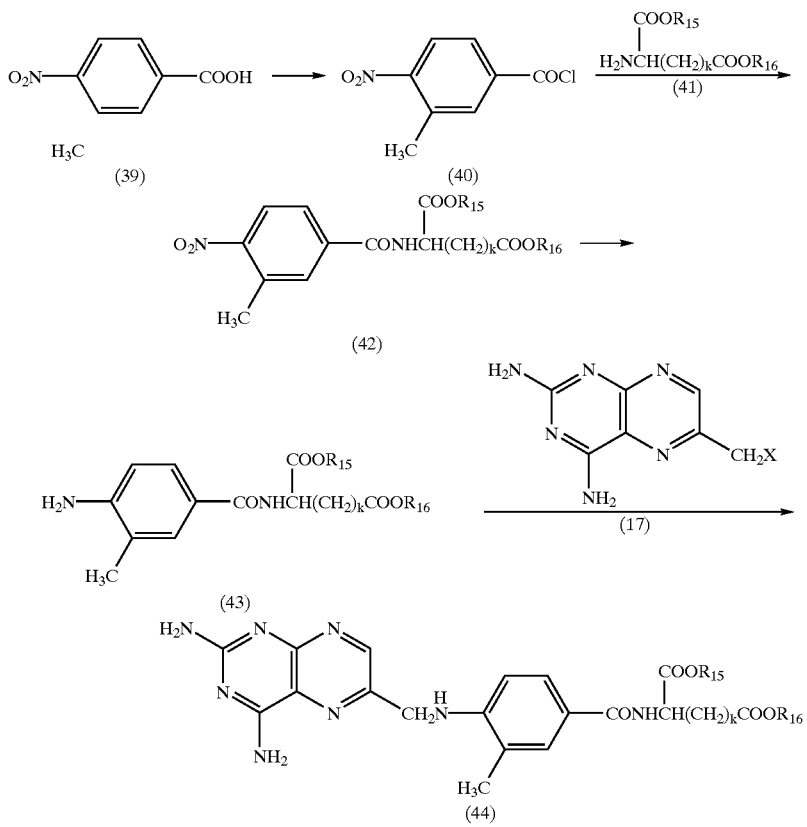

(where $R_{15}$, $R_{16}$ and k have the same meanings as defined above; and X is a halogen atom).

When implementing method A, the reaction for converting the compound of the general formula (1) to the compound of the general formula (2) is carried out by reacting the compound of the general formula (1) with a halogen of the formula $X_2$ in a solvent system composed of a mixture of water/methanol, water/ethanol, water/propanol or the like in the presence of a suitable reagent such as sodium hydrogen carbonate, calcium carbonate or potassium carbonate. Examples of the halogen represented by the general formula $X_2$ include fluorine, chlorine, bromine and iodine. If $R^2$ or $R^3$ in the compound of the general formula (1) is trifluoromethyl, the halogen to be reacted with is preferably iodine.

The reaction for converting the compound of the general formula (2) to the compound of the general formula (3) is carried out by reacting the compound of the general formula (2) with acetic anhydride in a solvent such as toluene, benzene, xylene, dioxane or pyridine. This reaction (acetylation) may be performed prior to the reaction for converting the compound of the general formula (1) to the compound of the general formula (2) (halogenation).

The reaction for converting the compound of the general formula (3) to the compound of the general formula (4) is carried out by reacting the compound of the general formula (3) with copper cyanide in a suitable solvent such as N-methylpyrrolidone, dimethylformamide, dimethylacetamide, dimethylpropylene urea or hexamethylphosphoric triamide.

The reaction for converting the compound of the general formula (4) to the compound of the general formula (5) is carried out by reacting the compound of the general formula (4) with a suitable reagent such as an aqueous solution of 12N HCl or 50% sodium hydroxide.

The reaction for producing the compound of the general formula (7) from the compounds of the general formulas (5) and (6) is carried out by reacting the two compounds in an alcohol such as methanol or ethanol in the presence of HCl or $H_2SO_4$. Alternatively, the reaction may be performed in an alcohol in the presence of thionyl chloride. Preferred examples of the alkyl group represented by R' in formulas (6) and (7) are methyl and ethyl.

The reaction for producing the compound of the general formula (9) from the compounds of the general formulas (7) and (8) is carried out by first dissolving the compound of the general formula (7) in a solvent such as pyridine or suspending it in tetrahydrofuran, dimethylformamide, dimethoxyethane, dioxane, toluene or the like in the presence of sodium hydride, then adding the compound of the general formula (8) and stirring the mixture. Examples of the protective group represented by $A^1$ in general formulas (8) and (9) include a p-toluenesulfonyl group, a benzyloxycarbonyl group and an acetyl group.

The reaction for producing the compound of the general formula (11) from the compounds of the general formulas (9) and (10) is carried out by first dissolving the compound of the general formula (9) in a suitable solvent such as anhydrous dimethylformamide, tetrahydrofuran, dimethoxyethane or dioxane, then adding a suitable reagent such as sodium hydride under cooling with ice, stirring the mixture at 10–120° C., preferably at room temperature, subsequently adding the compound of the general formula (10), and stirring the mixture at 10–120° C., preferably at room temperature.

The reaction for converting the compound of the general formula (11) to the compound of the general formula (12) is carried out by subjecting the compound of the general formula (11) to reaction in a solvent such as methanol, ethanol or tetrahydrofuran in the presence of a reagent such as an aqueous solution of potassium hydroxide or sodium hydroxide at 10–100° C., preferably at room temperature.

The reaction for converting the compound of the general formula (12) to the compound of the general formula (13) is carried out by first suspending the compound of the general formula (12) in an acid halide former such as thionyl chloride or oxalyl chloride and then stirring the suspension at room temperature in the presence of a catalytic amount of a reagent such as dimethylformamide.

The reaction for producing the compound of the general formula (15) from the compounds of the general formulas (13) and (14) is carried out by first dissolving the compound of the general formula (13) in a solvent such as dichloromethane, then adding the solution to an aqueous solution of the compound of the general formula (14) under cooling with ice or water, and stirring the mixture at room temperature in the presence of an inorganic base such as potassium carbonate, sodium hydroxide or sodium hydrogen carbonate.

The reaction for converting the compound of the general formula (15) to the compound of the general formula (16) is carried out by first dissolving anisole, phenol or the like in a solution of hydrogen bromide/acetic acid, then adding the compound of the general formula (15) to the resulting solution, and stirring the mixture at 10–60° C., preferably at room temperature. If $A^1$ is a carbobenzoxy group, the reaction of interest may be carried out by first dissolving the compound of the general formula (15) in a solvent such as methanol, ethanol or acetic acid, then adding palladium-carbon and subsequently stirring the solution in a hydrogen atmosphere at room temperature.

The reaction for producing the compound of the general formula (18) from the compounds of the general formulas (16) and (17) is carried out by stirring the two reactants in a solvent such as dimethylacetamide or dimethylformamide at 0–100° C., preferably at 50–60° C. In a special case where $R^4$ is a hydrogen atom, an aqueous solution of 1N sodium hydroxide may further be added to a solvent such as methanol, ethanol or tetrahydrofuran and the mixture is stirred at 0–60° C., preferably at 35° C., to yield the end compound.

When implementing method B, the reaction for producing the compound of the general formula (20) from the compounds of the general formulas (5) and (19) is carried out by reacting the compound of the general formula (5) with the compound of the general formula (19) in suspension at 0–100° C., preferably at room temperature. Examples of the protective group represented by $A^2$ in formula (19) include a trifluoroacetyl group and an acetyl group.

The reaction for producing the compound of the general formula (22) from the compounds of the general formulas (20) and (21) is carried out by first preparing an acetone solution of the two reactants, then adding potassium hydroxide to the solution, and stirring the mixture at 0–55° C., preferably at 45–53° C.

The reaction for converting the compound of the general formula (22) to the compound of the general formula (23) is carried out by reacting the compound of the general formula (22) with potassium hydroxide or sodium hydroxide in water. If desired, the compound of the general formula (22) may be replaced by the aforementioned compound of the general formula (11).

The reaction for producing the compound of the general formula (24) from the compounds of the general formulas (23) and (17) is carried out by stirring the two reactants in a solvent such as dimethylacetamide or dimethylformamide at 0–100° C., preferably at 40–55° C.

The reaction for producing the compound of the general formula (18) from the compounds of the general formulas (24) and (14) is carried out by first stirring the compound of general formula (24) in a solvent such as dimethylformamide, dimethylacetamide or N-methylpyrrolidinone in the presence of both diethyl cyanophosphonate or dicyclohexylcarbodiimide and 1-hydroxybenzotriazole or the like to prepare a corresponding active ester and mixed acid anhydride, then adding the compound of general formula (14) and stirring the mixture at 0–200° C., preferably at 10–80° C. Alternatively, triethylamine is added to the compound of general formula (24), then isobutyl chloroformate is added, and the mixture is stirred in a solvent such as dimethylformamide, dimethylacetamide or N-methylpyrrolidinone, followed by adding the compound of general formula (14) and stirring the mixture at –20 to 50° C., preferably at –10 to 0° C. If $R^4$ is a hydrogen atom, an aqueous solution of 1N sodium hydroxide is further added to a solvent such as methanol or ethanol and the mixture is stirred at 0–60° C., preferably at room temperature to yield the end product.

When implementing method C, the reaction for converting the compound of the general formula (25) to the compound of the general formula (26) is carried out by refluxing the compound of general formula (25) in acetic anhydride.

The reaction for converting the compound of the general formula (26) to the compound of the general formula (27) is typically carried out by reacting an acetic acid solution of the compound of general formula (26) with a halogen of the general formula $X_2$. Examples of the halogen $X_2$ include fluorine, chlorine, bromine and iodine.

The reaction for converting the compound of the general formula (27) to the compound of the general formula (28) is carried out by reacting the compound of general formula (27) with copper cyanide in a suitable solvent such as N-methylpyrrolidinone, dimethylformamide, dimethylacetamide, dimethylpropylene urea or hexamethylphosphoric triamide at 100–250° C., preferably at 200° C.

The reaction for converting the compound of the general formula (28) to the compound of the general formula (29) is carried out by reacting the compound of general formula (28) with a suitable reagent such as conc. HCl or an aqueous solution of 50% NaOH.

The reaction for producing the compound of the general formula (31) from the compounds of the general formulas (29) and (30) is typically carried out by first adding the compound of general formula (29) and ether to an aqueous solution of NaOH and then adding an ether solution of the compound of general formula (30) to the mixture. Examples of the protective group represented by $A^3$ in formulas (30) and (31) include a p-toluenesulfonyl group, a benzyloxycarbonyl group and an acetyl group.

The reaction for converting the compound of the general formula (31) to the compound of the general formula (32) is carried out by first suspending the compound of general formula (31) in an acid halide former such as thionyl chloride or oxalyl chloride and then stirring the suspension in the presence of a catalytic amount of dimethylformamide or the like at room temperature.

The reaction for producing the compound of the general formula (34) from the compounds of the general formulas (32) and (33) is carried out by first dissolving the compound of general formula (32) in a solvent such as dichloromethane, then adding an aqueous solution of the compound of general formula (33) and stirring the mixture at room temperature in the presence of an inorganic base such as potassium carbonate, sodium hydroxide or sodium hydrogen carbonate.

The reaction for converting the compound of the general formula (34) to the compound of the general formula (35) is carried out by first dissolving anisole, phenol or the like in a solution of hydrogen bromide/acetic acid, the n adding the compound of general formula (34) to the solution, and stirring the mixture at 10–60° C., preferably at room temperature. If $A^3$ is a carbobenzoxy group, the reaction of interest may be carried out by first dissolving the compound of general formula (34) in a solvent such as methanol, ethanol or acetic acid, then adding palladium-carbon to the solution and thereafter stirring the solution at room temperature in a hydrogen atmosphere.

The reaction for producing the compound of the general formula (36) from the compounds of the general formulas (35) and (17) is carried out by stirring the two reactants in a solvent such as dimethylacetamide or dimethylformamide at 0–100° C., preferably at 50–60° C. If $R_{12}$ and $R_{14}$ are each a hydrogen atom, an aqueous solution of 1N NaOH is further added to a solvent such as methanol, ethanol or tetrahydrofuran and the mixture is then stirred at 0–60° C., preferably at 35° C., to yield the end product.

The reaction for converting the compound of the general formula (36) to the compound of the general formula (37) is carried out by first dissolving the compound of general formula (36) in a solvent such as an aqueous solution of sodium hydrogen carbonate and then stirring the solution together with an aqueous solution of potassium nitrosodisulfonate. Alternatively, the compound of general formula (36) may be suspended in dioxane or the like and the suspension is stirred in the presence of dichlorodicyanobenzoquinone or the like. If desired, the compound of general formula (36) may be added to an acetic acid solution of manganese (III) acetate, followed by stirring the mixture.

When implementing method D, the reaction for producing the compound of the general formula (38) from the compounds of the general formulas (29) and (17) is carried out by stirring the two reactants in a solvent such as dimethylacetamide or dimethylformamide at 0–100° C., preferably at 40–55° C.

The reaction for producing the compound of the general formula (36) from the compounds of the general formulas (38) and (33) is carried out by first stirring the compound of general formula (38) in a solvent such as dimethylformamide, dimethylacetamide or N-methylpyrrolidinone in the presence of both diethyl cyanophosphonate or dicyclohexylcarbodiimide and 1-hydroxybenzotriazole, then adding the compound of general formula (33), and stirring the mixture at 0–200° C., preferably at 10–80° C. Alternatively, triethylamine is added to the compound of general formula (38), then isobutyl chloroformate is added, and the mixture is stirred in a solvent such as dimethylformamide, dimethylacetamide or N-methylpyrrolidinone; thereafter, the compound of general formula (33) is added and the mixture is stirred at –20 to 50° C., preferably at –10 to 0° C. If $R_{12}$ is a hydrogen atom, an aqueous solution of 1N NaOH is added to a solvent such as methanol or ethanol and the mixture is stirred at 0–60° C., preferably at room temperature to yield the end product.

When implementing method E, the reaction for converting the compound of the formula (39) to the compound of the formula (40) is carried out by suspending the compound of formula (39) in an acid halide former such as thionyl chloride or oxalyl chloride and then stirring the suspension at room temperature in the presence of a catalytic amount of dimethylformamide or the like.

The reaction for producing the compound of the general formula (42) from the compound of the formula (40) and the compound of the general formula (41) is carried out by first dissolving the compound of formula (40) in a solvent such as dichloromethane, then adding the compound of general formula (41) to the solution, and stirring the mixture at room temperature in the presence of both water and an inorganic base such as potassium carbonate, sodium hydroxide or sodium hydrogen carbonate.

The reaction for converting the compound of the general formula (42) to the compound of the general formula (43) is carried out by dissolving the compound of general formula (42) in a solvent such as acetic acid, then adding a zinc powder under cooling with ice, and stirring the mixture at room temperature.

The reaction under consideration may be carried out by using an iron powder in ethanol-HCl or performing catalytic reduction in a hydrogen atmosphere using palladium-carbon in methanol, ethanol or tetrahydrofuran.

The reaction for producing the compound of the general formula (44) from the compounds of the general formulas (43) and (17) is carried out by stirring the two reactants in a solvent such as dimethylacetamide or dimethylformamide at 0–100° C., preferably at 50–60° C. Examples of the halogen atom represented by X in the general formula (17) include chlorine and bromine. If $R_{15}$ is and $R_{16}$ are each a hydrogen atom, an aqueous solution of 1N NaOH is further added to a solvent such as methanol, ethanol or tetrahydrofuran and the mixture is stirred at 0–60° C., preferably at 20–30° C. to yield the end product.

The compounds of the general formula (II) thus produced in accordance with the present invention have antirheumatic action, which was verified by investigating the ability of the compounds to inhibit the proliferation of human peripheral blood derived lymphocytes in the experiment described below.

(Experiment)

Inhibition of the Proliferation of Human Peripheral Blood Derived Lymphocytes:

(Method)

Lymphocytes were separated from human peripheral blood by means of Ficoll-Paque$^R$. An adequately diluted drug under test and $10^5$ of the separated lymphocytes were cultivated in a 96-well culture plate for 2 days together with PHA (0.3 µg/ml). Five hours before the end of cultivation, $^3$H-UdR (1 µCi/well) was added and its uptake by the lymphocytes was measured with a scintillation counter (PHA: phytohaemagglutinin; UdR: deoxyuridine). The drugs under test were as follows:

Compound 1

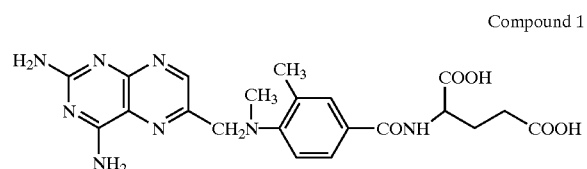

Compound 2

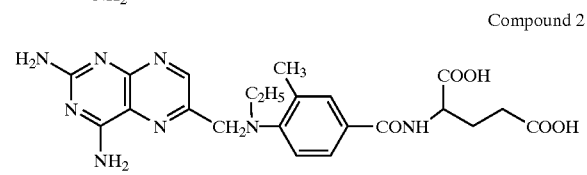

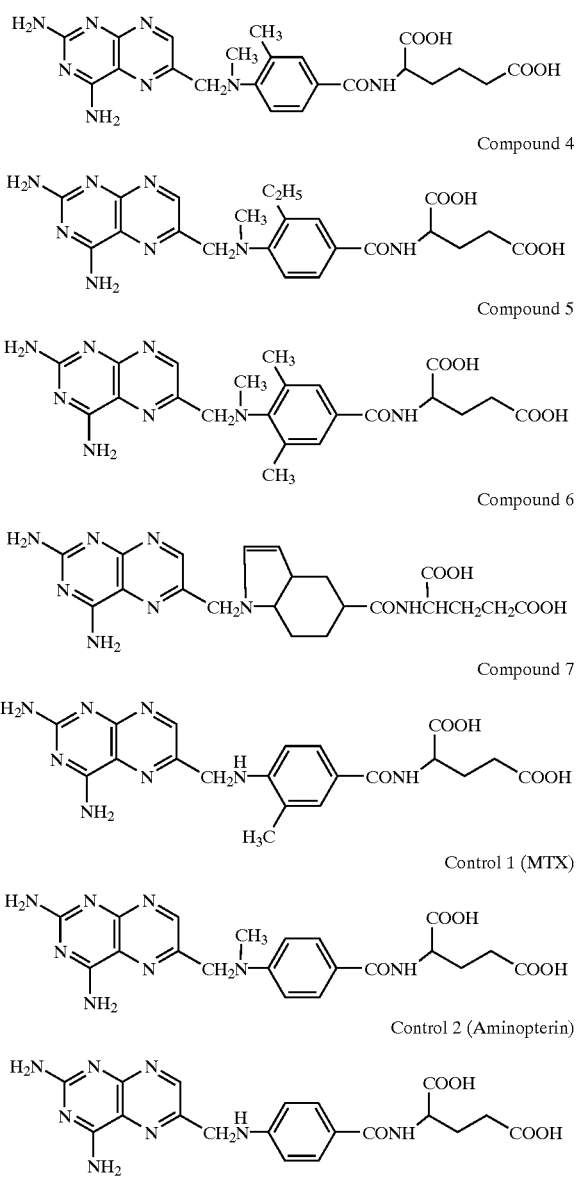

Compound 3, Compound 4, Compound 5, Compound 6, Compound 7, Control 1 (MTX), Control 2 (Aminopterin)

(Results and Discussion)

Figure 2:
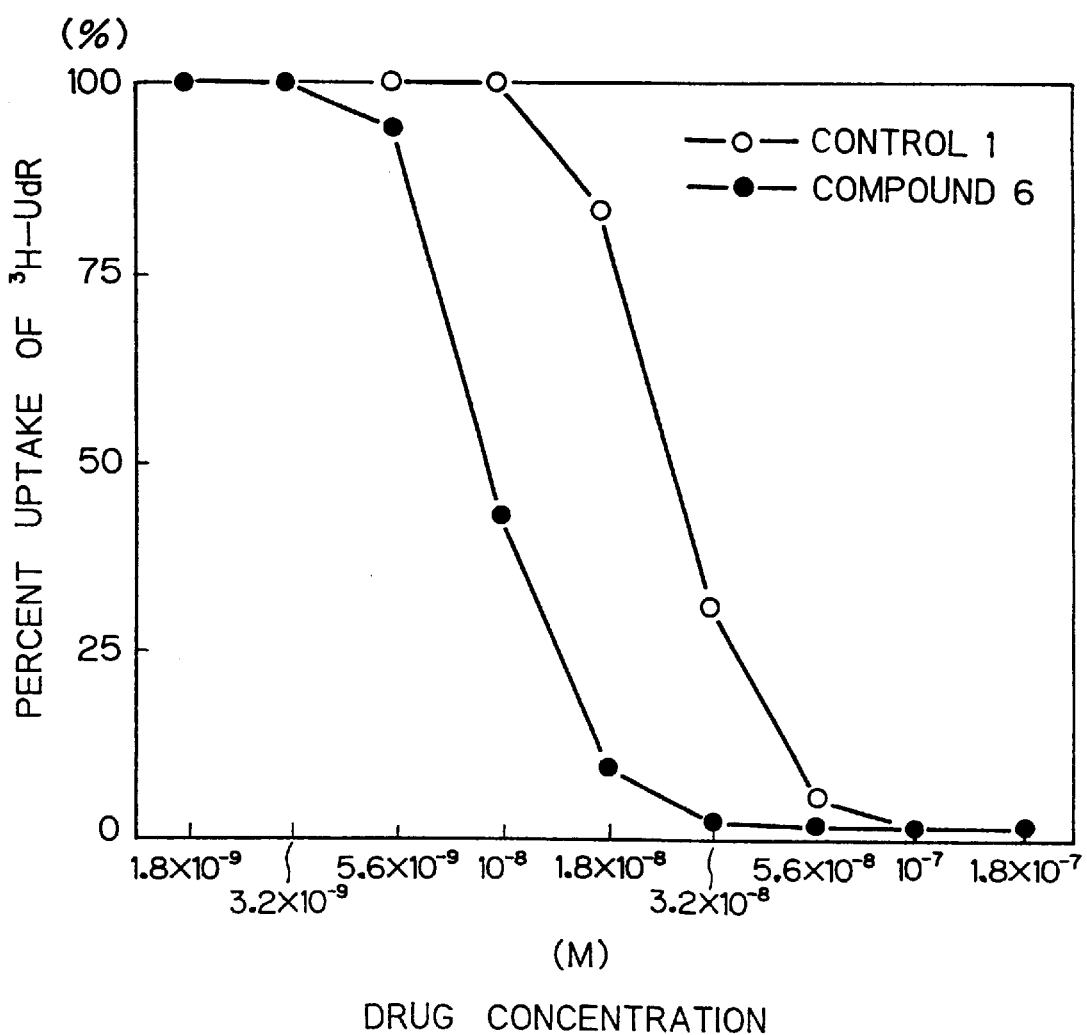
Figure 3:
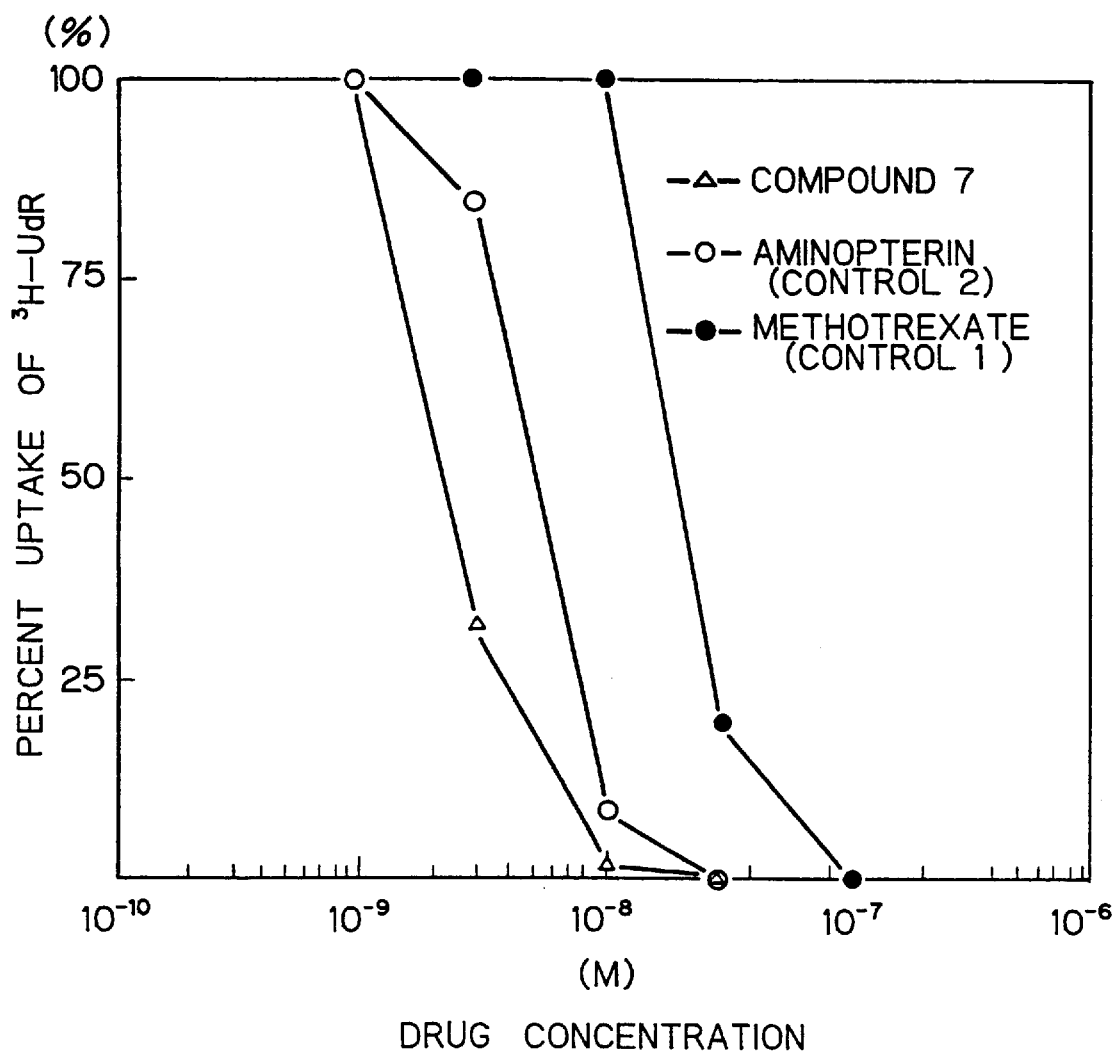

FIGS. 1, 2 and 3 show the percent uptakes of $^3$H-UdR by lymphocytes treated with the drugs under test, with 100% being assigned to the value of uptake by PHA stimulated lymphocytes in the absence of drugs. As is clear from FIGS. 1–3, the compounds of the present invention were found to be more effective in inhibiting the proliferation of lymphocytes (having better antirheumatic action) than the control compounds.

The following examples are provided for the purpose of further illustrating the present invention but are in no way to be taken as limiting.

REFERENCE EXAMPLE 1

Synthesis of N-Carbobenzoxy-4-amino-3-methylbenzoic Acid

4-Amino-3-methylbenzoic acid (5.0 g) was suspended in water (80 ml) and, thereafter, an ether solution (20 ml) of carbobenzoxychloride (3.7 g) and sodium hydrogen carbonate (3.6 g) were alternately added to the suspension under cooling with ice. Following stirring for 2.5 h at room temperature, an ether solution (95 ml) of carbobenzoxychloride (3.7 g) and sodium hydrogen carbonate (7.2 g) were further added alternately under cooling with ice, and the mixture was stirred for 1.5 h at room temperature. After rendering the reaction solution acidic with 4N HCl, the separating insoluble matter was recovered by filtration. The recovered solids were vacuum-dried to yield the end product (2.8 g).

| | |
|---|---|
| $^1$H-NMR(CD$_3$COCD$_3$, δ): | 2.38(3H, s), 5.20(2H, s), 7.41(5H, m), 7.97(3H, m) |

REFERENCE EXAMPLE 2

Synthesis of Methyl N-Carbobenzoxy-N-methyl-4-amino-3-methylbenzoate

Sodium hydride (1.4 g) was suspended in dimethylformamide (10 ml) and, thereafter, a dimethylformamide solution (10 ml) of the compound synthesized in Reference Example 1 (2.8 g) was added slowly to the suspension at 0° C. After stirring the reaction solution for 1 h at room temperature, methyl iodide was added slowly and the mixture was stirred at room temperature for 2 h. Then, the reaction solution was poured into a saturated aqueous solution of sodium hydrogen carbonate and the mixture was subjected to extraction with toluene. The organic layer was dried with sodium sulfate and the solvent was distilled off under vacuum. The resulting residue was subjected to silica gel column chromatography and eluted with chloroform to yield the end product (1.8 g).

| | |
|---|---|
| $^1$H-NMR(CDCl$_3$, δ): | 2.18(3H, s), 3.22(3H, s), 3.89(3H, s), 5.10(2H, s), 7.21(6H, m), 7.90(2H, m) |

REFERENCE EXAMPLE 3

Synthesis of N-Carbobenzoxy-N-methyl-4-amino-3-methylbenzoic Acid

An aqueous solution (15 ml) of 2N NaOH was added to an ethanol (15 ml) solution of the compound (1.8 g) synthesized in Reference Example 2 and the mixture was refluxed for 2 h. Subsequently, the reaction solution was concentrated to 10 ml under vacuum. After the concentrate was rendered acidic with 4N HCl, it was subjected to extraction with chloroform and the extract was dried with sodium sulfate. The solvent was distilled off under vacuum to yield the end product (1.5 g).

| | |
|---|---|
| $^1$H-NMR(CDCl$_3$, δ): | 2.20(3H, s) , 3.24(3H, s), 5.12(2H, s), 6.91–7.56(6H, m), 7.74–8.12(2H, m) |

REFERENCE EXAMPLE 4

Synthesis of Diethyl N-(N'-Carbobenzoxyl-N'-methyl-4-amino-3-methylbenzoyl)-L-glutamate The compound (820 mg) synthesized in Reference Example 3 was added to thionyl chloride (5 ml); thereafter, a catalytic amount of dimethylformamide was further added and the mixture was stirred for 2 h at room temperature. Subsequently, the reaction solution was concentrated to dryness under vacuum. The resulting solids was dissolved in dichloromethane (20 ml) and diethyl glutamate HCl (700 mg) and potassium carbonate (1.4 g) were added to the solution; after adding water (20 ml) the mixture was stirred vigorously at room temperature for 12 h. Then, the reaction solution was poured into water and subjected to extraction with chloroform. The organic layer was washed with 1N HCl and dried with sodium sulfate. The solvent was distilled off under vacuum. The resulting residue was subjected to silica gel column chromatography and eluted with a solvent system composed of chloroform and methanol (100:3) to yield the end product (700 mg).

$^1$H-NMR(CDCl$_3$, δ): 1.1–1.5(6H, m), 2.0–2.7(4H, m), 2.18(3H, s), 3.19(3H, s), 3.9–4.4(4H, m), 4.80(1H, m), 5.10(2H, s), 7.0–7.5(6H, m), 7.63(2H, m)

REFERENCE EXAMPLE 5

Synthesis of Diethyl N-[N'-Methyl-(4-amino-3-methylbenzoyl)]-L-glutamate

The compound (700 mg) synthesized in Reference Example 4 was added to a solution containing anisole (700 mg) in 30% hydrogen bromide/acetic acid (7 ml) and the mixture was stirred at room temperature for 4 h. Subsequently, ether (200 ml) was added to the reaction solution, whereupon a reddish brown oil was precipitated. With the greater part of the ether layer being removed, the oil was suspended in chloroform and the resulting suspension was washed with a saturated solution of sodium hydrogen carbonate to recover the organic layer by separation. The organic layer was then dried with sodium sulfate and the solvent was distilled off under vacuum to yield the end product (360 mg).

$^1$H-NMR(CDCl$_3$, δ): 1.0–1.5(6H, m), 2.11(3H, s), 2.90(3H, s), 2.1–2.7(4H, m), 3.9–4.4(4H, m), 4.80(1H, m), 6.54(1H, d, J=8Hz), 6.80(1H, d, J=7Hz), 7.61(2H, m)

EXAMPLE 1

Synthesis of Diethyl N-{4-[N'-(2,4-Diamino-6-pteridinyl)methyl-N'-methylamino]-3-methylbenzoyl}-L-glutamate The compound (360 mg) synthesized in Reference Example 5 and an isopropanol adduct of 6-bromomethyl-2,4-diaminopteridine hydrobromide (407 mg) were suspended in dimethylacetamide (6 ml) and the suspension was stirred at 55–60° C. for 4 h. To the cooled reaction solution, water (30 ml) containing triethylamine (248 mg) was added and the mixture was stirred, followed by extraction with chloroform. The chloroform layer was dried with sodium sulfate and the solvent was distilled off under vacuum. The resulting residue was subjected to silica gel column chromatography and eluted with a solvent system consisting of chloroform and methanol (10:1) to yield the end product (280 mg).

$^1$H-NMR(CDCl$_3$, δ): 1.2–1.4(6H, m), 2.0–2.6(4H, m), 2.41(3H, s), 2.73(3H, s), 4.0–4.3(4H, m), 4.32(2H, s), 4.76(1H, m), 7.06(1H, d, J=8.3Hz), 7.41(1H, d, J=7.8Hz), 7.65(2H, m), 8.79(1H, s)

EXAMPLE 2

Synthesis of N-{4-[N'-(2,4-Diamino-6-pteridinyl)methyl-N'-methylamino]-3-methylbenzoyl}-L-glutamic Acid (Compound 1)

An aqueous solution of 1N NaOH (1.6 ml) was added to an ethanol (20 ml) solution of the compound (280 mg) synthesized in Example 1 and the mixture was stirred at 35° C. for 4 h. Following stirring at 25° C. for 20 h, water (2 ml) was added to the reaction solution, which was then evaporated to dryness under vacuum, with care being taken so that the external temperature would not exceed 30° C. The resulting yellow solids was dissolved in water (10 ml) and the solution was adjusted to pH of 3.7 with 1N HCl, followed by standing in a refrigerator for 2 h. The separating precipitate was recovered by filtration to yield the end product (180 mg).

$^1$H-NMR(DMSO-d$_6$, δ): 1.9–2.2(2H, m), 2.35(2H, t, J=8.0Hz), 2.42(3H, s), 2.73(3H, s), 4.34(2H, s), 4.41(1H, m), 7.10(1H, d, J=8.3Hz), 7.72(2H, m), 8.38(1H, d, J=7.8Hz), 8.65(1H, s)

REFERENCE EXAMPLE 6

Synthesis of Ethyl N-Carbobenzoxy-N-ethyl-4-amino-3-methyl-benzoate

Sodium hydride (164 mg) was suspended in dimethylformamide (2 ml) in a nitrogen atmosphere and the temperature was adjusted to 0° C. To the suspension, a dimethylformamide solution (2 ml) of N-benzyloxycarbonyl-4-amino-3-methylbenzoic acid (650 mg) was added slowly and, thereafter, ethyl iodine (730 μl) was added slowly at 0° C. Following stirring at room temperature for 2.5 h, the reaction solution was poured to a saturated solution of sodium hydrogen carbonate and the mixture was subjected to extraction with toluene. The toluene layer was dried with magnesium sulfate and the solvent was distilled off under vacuum to yield the end product (680 mg).

$^1$H-NMR(CDCl$_3$, δ): 0.91–1.63(6H, m), 2.16(3H, s), 3.35–3.90(2H, m), 4.10–4.55(2H, m), 5.07(2H, bs), 6.95–7.35(6H, m), 7.68–7.95(2H, m)

REFERENCE EXAMPLE 7

Synthesis of N-Benzyloxycarbonyl-N-ethyl-4-amino-3-methylbenzoic Acid

An aqueous solution (5 ml) of 2N NaOH was added to an ethanol (5 ml) solution of the compound (680 mg) synthesized in Reference Example 6 and the mixture was refluxed for 2 h. Then, the reaction solution was cooled to room temperature and evaporated to dryness under vacuum. The resulting residue was dissolved in a small amount of water and the solution was washed with ether, followed by pH adjustment to 3 with conc. HCl. The separating precipitate was subjected to extraction with chloroform and dried with sodium sulfate. The solvent was distilled off under vacuum to yield the end product (540 mg).

| | |
|---|---|
| $^1$H-NMR(CDCl$_3$, δ): | 1.16(3H, t, J=5.4Hz), 2.20(3H, s), 3.38–3.94(2H, m), 5.12(2H, bs), 6.93–7.44(6H, m), 7.72–8.08(2H, m) |

REFERENCE EXAMPLE 8

Synthesis of Diethyl N-[N'-Ethyl-3-methyl-(4-aminobenzoyl)]-L-glutamate

The compound (500 mg) synthesized in Reference Example 7 was added to thionyl chloride (3 ml) and a catalytic amount of dimethylformamide was added to the mixture followed by stirring at room temperature for 2 h. Then, the reaction solution was concentrated to dryness under vacuum. The resulting solids was dissolved in dichloromethane (13 ml) and to the solution, diethyl glutamate ester (382 mg), potassium carbonate (448 mg) and water (13 ml) were added, followed by vigorous stirring at room temperature for 12 h. The reaction solution was poured into a saturated aqueous solution of sodium hydrogen carbonate and the mixture was subjected to extraction with chloroform, followed by washing with 1N HCl and drying with sodium sulfate. The solvent was distilled off under vacuum to yield a colorless oil (830 mg). Then, a liquid mixture of 30% hydrogen bromide/acetic acid (10 ml) and anisole (830 mg) was added to the resulting residue, followed by stirring at room temperature for 3 h. After the reaction, a large amount of ether was added to the reaction solution, whereupon a dark brown oil was precipitated. The greater part of the ether layer was removed and the oil was suspended in chloroform, with the suspension being washed with a saturated aqueous solution of sodium hydrogen carbonate. The organic layer was recovered by separation and dried with magnesium sulfate, followed by distilling off the solving to yield the end product (360 mg).

| | |
|---|---|
| $^1$H-NMR(CDCl$_3$, δ): | 1.03–4.18(9H, m), 1.83–2.62(7H, m), 2.96–3.43(2H, m), 3.83–4.40(4H, m), 4.48–4.98(1H, m), 6.33–6.92(2H, m) 7.34–7.73(2H, m) |

EXAMPLE 3

Synthesis of Diethyl N-{4-[N'-(2,4-Diamino-6-pteridinyl)methyl-N'-ethylamino]-3-methylbenzoyl}-L-glutamate A dimethylacetamide suspension (10 ml) of the compound (360 mg) synthesized in Reference Example 8 and an isopropanol adduct of 6-bromethyl-2,4-diaminopteridine hydrobromide (342 mg) was stirred at 60° C. for 4 h; an isopropanol adduct of 6-bromomethyl-2,4-diaminopteridine hydrobromide (342 mg) was further added and the mixture was stirred at 70° C. for 1.5 h. Then, the reaction solution was poured into a saturated aqueous solution of sodium hydrogen carbonate and the mixture was subjected to extraction with chloroform. The chloroform layer was dried with magnesium sulfate and the solvent was distilled off under vacuum. The resulting residue was subjected to silica gel column chromatography and elution was conducted with a solvent system of chloroform and methanol (10:1) to yield the end product (167 mg).

| | |
|---|---|
| $^1$H-NMR(CDCl$_3$, δ): | 1.06(3H, t, J=8.0Hz), 1.15–1.42(6H, m), 1.76(3H, s), 2.37–2.54(4H, m), 3.08(2H, q, J=8.0Hz), 4.10(2H, q, J=8.0Hz), 4.24(2H, q, J=8.0Hz), 4.38(2H, s), 4.70–4.88(1H, m), 5.32(2H, bs), 6.94(1H, d, J=7.4Hz), 7.05(1H, d, J=8.8Hz), 7.56(1H, d, J=5.2Hz), 7.67(1H, bs), 8.80(1H, s) |

EXAMPLE 4

Synthesis of N-{4-[N'-(2,4-Diamino-6-pteridinyl)methyl-N'-ethylamino]-3-methylbenzoyl}-L-glutamic Acid (Compound 2)

An aqueous solution (0.84 ml) of 1N NaOH was added to an ethanol solution (11 ml) of the compound (150 mg) synthesized in Example 3 and the mixture was stirred at 35° C. for 4 h. Following further stirring at 25° C. for 20 h, water (1 ml) was added to the reaction solution, which was evaporated to dryness under vacuum, with care being taken so that the external temperature would not exceed 30° C. The resulting yellow solids was dissolved in water (5 ml) and the solution was adjusted to pH of 3.7 with 1N HCl, followed by standing in a refrigerator for 2 h. The separating precipitate was recovered by filtration to yield the end product (121 mg).

| | |
|---|---|
| $^1$H-NMR(DMSO-d$_6$, δ): | 1.04(3H, t, J=6.8Hz), 1.85–2.28(2H, m), 2.30–2.48(5H, m), 3.04(2H, q, J=6.8Hz), 4.39(2H, s), 6.57(2H, bs), 7.10(1H, d, J=8.3Hz), 7.61(1H, d, J=8.3Hz), 7.72(1H, s), 8.34(1H, d, J=7.8Hz), 8.57(1H, s) |

REFERENCE EXAMPLE 9

Synthesis of Dimethyl-N-(N'-Carbobenzoxy-N'-methyl-4-amino-3-methylbenzoyl)-L-2-aminoadipate The compound (8.4 g) synthesized in Reference Example 3 was added to thionyl chloride (29 ml) and a catalytic amount of dimethylformamide was further added, with the mixture being stirred at room temperature for 2 h. Then, the reaction solution was concentrated to dryness under vacuum. The resulting solids was dissolved in dichloromethane (150 ml) and to the solution, dimethyl L-2-aminoadipate ester HCl (6.6 g), potassium carbonate (10 g) and water (150 ml) were added, followed by vigorous stirring at room temperature for 12 h. The reaction solution was poured into water and the mixture was subjected to extraction with chloroform, followed by washing with 1N HCl and drying with sodium sulfate. The solvent was distilled off under vacuum. The resulting residue was subjected to silica gel column chromatography and elution was conducted with a solvent system of chloroform and methanol (100:3) to yield the end product (9.7 g).

| $^1$H-NMR(CDCl$_3$, δ): | 1.45–2.55(9H, m), 3.15(3H, s), 3.60(3H, s), 3.72(3H, s), 4.45–4.95(1H, m), 5.05(2H, bs), 6.80–7.35(7H, m), 7.45–7.95(2H, m) |
|---|---|

REFERENCE EXAMPLE 10

Synthesis of Dimethyl N-[N'-Methyl(4-amino-3-methylbenzoyl)]-L-2-aminoadipate The compound (9.5 g) synthesized in Reference Example 9 was added to a solution having anisole (9.5 g) contained in 30% hydrogen bromide/acetic acid (100 ml) and the mixture was stirred at room temperature for 4 h. Subsequently, a large amount of ether was added to the reaction solution, whereupon a reddish brown oil was precipitated. The greater part of the ether layer was removed and the oil was suspended in chloroform, with the suspension being washed with a saturated aqueous solution of sodium hydrogen carbonate and subjected to extraction with chloroform. The chloroform layer was dried with sodium sulfate and the solvent was distilled of under vacuum to yield the end product (4.0 g).

| $^1$H-NMR(CDCl$_3$, δ): | 1.43–2.00(4H, m), 2.03(3H, s), 2.34(2H, t, J=6Hz), 2.90(3H, s), 3.63(3H, s), 3.73(3H, s), 4.53–5.03(1H, m), 6.33–6.80(2H, m), 7.38–7.68(2H, m) |
|---|---|

EXAMPLE 5

Synthesis of Dimethyl N{4-[N'-(2,4-Diamino-6-pteridinyl)methyl-N'-methylamino]-3-methyl}benzoyl-L-2-aminoadipate The compound (3.83 g) synthesized in Reference Example 10 and an isopropanol adduct of 6-bromomethyl-2,4-diaminopteridine hydrobromide (4.06 g) were suspended in dimethylacetamide (75 ml) and the suspension was stirred at 55–60° C. for 4 h. After cooling, the reaction solution was poured into a saturated aqueous solution of sodium hydrogen carbonate and the mixture was subjected to extraction with chloroform. The chloroform layer was dried with sodium sulfate and the solvent was distilled off under vacuum. The resulting residue was subjected to silica gel column chromatography and elution was conducted with a solvent system of chloroform and methanol (10:1) to yield the end product (3.41 g).

| $^1$H-NMR(CDCl$_3$, δ): | 1.55–1.95(4H, m), 2.26–2.46(5H, m), 2.74(3H, s), 3.67(3H, s), 3.79(3H, s) 4.33(2H, s), 4.70–4.85(1H, m), 5.34(2H, bs), 6.78(1H, d, J=6.8Hz), 7.05(1H, d, J=8.4Hz), 7.61(1H, d, J=7.8Hz), 7.68(1H, s), 8.85(1H, s) |
|---|---|

EXAMPLE 6

Synthesis of N-{4-[N'-(2,4-Diamino-6-pteridinyl)methyl-N'-methylamino]-3-methyl}benzoyl-L-2-aminoadipic Acid (Compound 3)

An aqueous solution (18 ml) of 1N NaOH was added to an ethanol (160 ml) solution of the compound (3.0 g) synthesized in Example 5 and the mixture was stirred at 35° C. for 4 h. Following further stirring at 25° C. for 20 h, water (20 ml) was added to the reaction solution, which was evaporated to dryness under vacuum, with care being taken so that the external temperature would not exceed 30° C. The resulting yellow solids was dissolved in water (50 ml) and the solution was adjusted to pH of 3.7 with 1N HCl, followed by standing in a refrigerator for 2 h. The separating precipitate was recovered by filtration to yield the end product (2.3 g).

| $^1$H-NMR(DMSO-d$_6$, δ): | 1.40–1.88(4H, m), 2.24(2H, t, J=7.8Hz), 2.41(3H, s), 2.72(3H, s), 4.23–4.43(4H, m), 6.64(2H, bs), 7.11(1H, d, J=8.8Hz), 7.66(1H, d, J=8.3Hz), 7.74(1H, s), 8.38(1H, d, J=8.2Hz), 8.64(1H, s) |
|---|---|

REFERENCE EXAMPLE 11

Synthesis of 4–2,4-[N'-(Diamino-6-pteridinyl)methyl]-N'-methylamino-3-methylbenzoic Acid An isopropanol adduct of 6-bromomethyl-2,4-diaminopteridine hydrobromide (3.8 g) and 4-methylamino-3-methylbenzoic acid (4.8 g) were suspended in dimethylacetamide (50 ml) in a nitrogen atmosphere and the suspension was stirred at 40° C. for 4 days, followed by stirring at 55° C. for 2 days. The reaction solution was poured into water (500 ml) and the mixture was adjusted to pH of 5 with 1N NaOH. The resulting precipitate was recovered by filtration and washed with water and acetone to yield the end product (3.3 g).

| $^1$H-NMR(DMSO-d$_6$, δ): | 2.40(3H, s), 2.74(3H, s), 4.36(2H, s), 7.10(1H, d, J=8.3Hz), 7.6–7.8(2H, m), 8.64(1H, s) |
|---|---|

EXAMPLE 7

Synthesis of N-{4-[N'-(2,4-Diamino-6-pteridinyl)methyl-N'-methylamino]-3-methyl}benzoyl-L-homocysteic Acid Ammonium Salt Triethylamine (2.7 ml) and isobutyl chloroformate (0.85 ml) were added, in a nitrogen atmosphere, to a dimethylacetamide (250 ml) suspension of the compound (2.4 g) synthesized in Reference Example 11, and the mixture was stirred for 5 min. Isobutyl chloroformate (0.12 ml) was further added and the mixture was stirred for 5 min. To the resulting solution, methyl L-homocystate HCl (1.5 g) was added and the mixture was stirred for 30 min. Thereafter, triethylamine (1.35 ml), isobutyl chloroformate (0.42 ml) and methyl L-homocystate HCl (0.75 g) were added in a similar manner and the mixture was stirred for 30 min. The temperature of the mixture was raised slowly to room temperature and it was stirred for 45 min. Thereafter, the solvent was distilled off under vacuum with care being taken so that the temperature of the bath would not exceed 40° C., and an aqueous solution of 0.1N NaOH (400 ml) was added to the residue, with the mixture being stirred for 2 h at room temperature. Thereafter, an aqueous solution of 1N NaOH (8 ml) was further added and the mixture was stirred for 20 min. The reaction solution was freeze-dried and the resulting residue was subjected to silica gel column chromatography and elution was conducted with a solvent system of chloroform, methanol and aqueous ammonia (5:4:1). The resulting crude product was further loaded on DEAE cellulose column, washed with water and eluted with an aqueous solution of 3% ammonium bicarbonate, yielding the end product (1.1 g).

$^1$H-NMR(D$_2$O, δ): 2.15–2.25(1H, m), 2.3–2.4(1H, m), 2.4(3H, s), 2.8(3H, s), 2.9–3.1(2H, m), 4.4–4.5(1H, m), 4.5(2H, s), 7.1(1H, d, J=8.5Hz), 7.6(1H, d, J=8.5Hz), 7.7(1H, m), 8.6(1H, s)

REFERENCE EXAMPLE 12

Synthesis of Methyl N-p-Toluenesulfonyl-4-amino-3-ethylbenzoate

Para-toluenesulfonyl chloride (3 g) was added to a pyridine (30 ml) solution of methyl 3-ethyl-4-aminobenzoate ester (1.86 g) and the mixture was stirred at room temperature for 3 h. After the reaction, the solvent was distilled off under vacuum and both chloroform and 1N HCl were added to the residue. Following stirring, the organic layer was recovered by separation. The organic layer was dried with magnesium sulfate and the solvent was distilled off under vacuum. The resulting residue was subjected to silica gel column chromatography and elution was conducted with a solvent system of hexane and ethyl acetate (4:1), yielding the end product (3 g).

$^1$H–NMR (CDCl$_3$, δ): 1.10(3H, t), 2.40(3H, s), 2.1–2.8(2H, m), 3.90(3H, s), 6.6–7.9(7H, m)

REFERENCE EXAMPLE 13

Synthesis of Methyl N-p-Toluenesulfonyl-N-methyl-4-amino-3-ethylbenzoate

Sodium hydride (1.3 g) was added, under cooling with ice, to an anhydrous dimethylformamide (50 ml) solution of the compound (3 g) synthesized in Reference Example 12 and the mixture was stirred at room temperature for 10 min. Then, methyl iodide (3.8 g) was added to the reaction solution and the mixture was reverted to room temperature, followed by stirring for 2 h. After the reaction, water was added to the reaction solution and the mixture was subjected to extraction with ethyl acetate. The ethyl acetate layer was dried with magnesium sulfate and the solvent was distilled off under vacuum. The resulting residue was subjected to silica gel column chromatography and elution was conducted with solvent chloroform, yielding the end product (1.56 g).

$^1$H–NMR (CDCl$_3$, δ): 1.25(3H, t), 2.45(3H, s), 2.7–3.1(2H, m), 3.15(3H, s), 3.90(3H, s), 6.6–8.1(7H, m)

REFERENCE EXAMPLE 14

Synthesis of N-p-Toluenesulfonyl-N-methyl-4-amino-3-ethylbenzoic Acid

An aqueous solution of 1N NaOH (60 ml) was added to a methanol (60 ml) solution of the compound (1.56 g) synthesized in Reference Example 13 and the mixture was stirred under reflux for 2 h. With the temperature of the water bath held below 30° C., the solvent was concentrated under vacuum. The reaction solution was adjusted to pH of 2.5 by addition of 1N HCl and the separating precipitate was recovered by filtration to yield the end product (1.33 g).

$^1$H–NMR (CDCl$_3$, δ): 1.25(3H, t), 2.45(3H, s), 2.7–3.1(2H, m), 3.15(3H, s), 6.6–8.2(7H, m)

REFERENCE EXAMPLE 15

Synthesis of Diethyl N-(N'-p-Toluenesulfonyl-N'-methyl-4-amino-3-ethylbenzoyl)-L-glutamate The compound (1.33 g) synthesized in Reference Example 14 was added to thionyl chloride (5 ml) and, following the addition of dimethylformamide in a catalytic amount, the mixture was stirred at room temperature for 2 h. Subsequently, the reaction solution was concentrated to dryness under vacuum. The resulting solids was dissolved in dichloromethane (35 ml) and to the solution, diethyl glutamate HCl (900 mg), potassium carbonate (1.4 g) and water (15 ml) were added. The mixture was stirred vigorously overnight at room temperature. The reaction solution was poured into water and the mixture was subjected to extraction with chloroform. The chloroform layer was washed with a saturated aqueous solution of sodium hydrogen carbonate and 1N HCl, then dried with magnesium sulfate. The solvent was distilled off under vacuum to yield the end product (1.5 g).

$^1$H–NMR (CDCl$_3$, δ): 1.0–1.4(9H, m), 2.0–3.0(6H, m), 2.45(3H, s), 3.10(3H, s), 3.9–4.4(4H, m), 4.5–5.0(1H, m), 6.5–7.9(7H, m)

REFERENCE EXAMPLE 16

Synthesis of Diethyl N-(N'-Methyl-4-amino-3-ethylbenzoyl)-L-glutamate

The compound (1.5 g) synthesized in Reference Example 15 was added to a solution of anisole (1.5 g) in 30% hydrogen bromide/acetic acid (15 ml) and the mixture was stirred at room temperature for 4.5 h. Subsequently, ether (300 ml) was added to the reaction solution, whereupon a reddish brown oil was precipitated. The greater part of the ether layer was removed and the oil was suspended in chloroform. The suspension was then washed with a saturated aqueous solution of sodium hydrogen carbonate and, thereafter, the organic layer was recovered by separation. The separated organic layer was dried with magnesium sulfate and the solvent was distilled off under vacuum to yield the end product (1.0 g).

$^1$H–NMR (CDCl$_3$, δ): 1.0–1.4(9H, m), 2.0–3.0(6H, m), 2.85(3H, s), 3.7–4.3(4H, m), 4.5–4.9(1H, m), 6.4–7.7(3H, m)

EXAMPLE 8

Synthesis of Diethyl N-{4-[N'-(2,4-Diamino-6-pteridinyl)methyl-N'-methylamino]-3-ethylbenzoyl}-L-glutamate The compound (1.0 g) synthesized in Reference Example 16 and an isopropanol adduct of 6-bromomethyl-2,4- diaminopteridyl hydrobromide (1.1 g) were suspended in dimethylacetamide (10 ml) and the suspension was stirred at 60° C. for 6 h. After cooling, the reaction solution was poured into a saturated aqueous solution of sodium hydrogen carbonate and the mixture was subjected to extraction with chloroform. The organic layer was dried with magnesium sulfate and the solvent was distilled off under vacuum. The resulting residue was subjected to silica gel column chromatography and elution was conducted with a solvent system of chloroform and methanol (10:1), yielding the end product (671 mg).

$^1$H–NMR (CD$_3$OD, δ): 1.0–1.4(9H, m), 2.0–3.0(6H, m), 2.75(3H, s), 3.9–4.7(7H, m), 7.1–7.8(3H, m), 8.70(1H, s)

EXAMPLE 9

Synthesis of N-{4-[N'-(2,4-Diamino-6-pteridinyl)methyl-N'-methylamino]-3-ethylbenzoyl}-L-glutamic Acid (Compound 4)

An aqueous solution of 1N NaOH (1.78 ml) was added to an ethanol (22 ml) solution of the compound (640 mg) synthesized in Example 8 and the mixture was stirred at 35° C. for 4.5 h. Following further stirring at 25° C. for 20 h, water (2 ml) was added to the reaction solution and, then, the reaction solution was adjusted to pH of 3.7 with 1N HCl, followed by standing overnight in a cool place. The separating precipitate was recovered by filtration to yield the end product (340 mg).

$^1$H–NMR (DMSO-d$_6$, δ): 1.28(3H, m), 1.9–2.5(4H, m), 2.69(3H, s), 2.80(2H, m), 4.29(2H, s), 4.39(1H, m), 7.22(1H, m), 7.71(2H, m), 8.64(1H, s)

REFERENCE EXAMPLE 17

Synthesis of Ethyl N-Carbobenzoxy-4-amino-3,5-dimethylbenzoate

Ethyl 4-amino-3,5-dimethylbenzoate (2.0 g) was added to a tetrahydrofuran (THF) suspension of sodium hydride (0.82 g) in a nitrogen atmosphere and the mixture was stirred at room temperature for 30 min. Subsequently, carbobenzoxychloride (4.4 ml) was added to the suspension and the mixture was stirred overnight. A small amount of water was added to the reaction solution and the mixture was poured into ice water, followed by extraction with ethyl acetate. Following washing and drying (with magnesium sulfate), the solvent was distilled off under vacuum. The resulting crystal was recovered by filtration in the presence of ethanol and dried under vacuum to yield the end product (3.2 g).

$^1$H–NMR (CDCl$_3$, δ): 1.39(3H, t, J = 7 Hz), 2.05(6H, s), 4.35(2H, q, J = 7 Hz), 5.15(2H, s), 7.23(5H, m), 7.75(2H, s)

REFERENCE EXAMPLE 18

Synthesis of Ethyl N-Carbobenzoxy-N-methyl-4-amino-3,5-dimethylbenzoate

Sodium hydride (1.2 g) was suspended in dimethylformamide (50 ml) in a nitrogen atmosphere and the suspension was stirred. The compound (3.2 g) synthesized in Reference Example 17 was added to the suspension at room temperature, followed by stirring for 30 min. Then, methyl iodide (1.8 ml) was added, followed by further stirring overnight at room temperature. Subsequently, a few drops of water were added to the reaction solution under cooling with ice and the reaction solution was poured into ice water. The mixture was subjected to extraction with ethyl acetate and dried with magnesium sulfate. The solvent was distilled off under vacuum and the resulting residue was subjected to silica gel column chromatography, followed by elution with a solvent system of hexane and ethyl acetate (9:1) to yield the end product (1.47 g).

$^1$H–NMR (CDCl$_3$, δ): 1.38(3H, t, J = 7 Hz), 2.21(6H, s), 3.17(3H, s), 4.42(2H, q, J = 7 Hz), 5.13(2H, s), 7.0–7.6(5H, m), 7.80(2H, s)

REFERENCE EXAMPLE 19

Synthesis of N-Carbobenzoxy-N-methyl-4-amino-3,5-dimethylbenzoic Acid

An aqueous solution of 1N NaOH (12 ml) was added to a THF (30 ml) solution of the compound (1.47 g) synthesized in Reference Example 18 and the mixture was heated at 60° C. for 6 h, followed by further stirring overnight at room temperature. Then, the reaction solution was adjusted to pH of ca. 5 with 3N HCl and concentrated under vacuum. After pH adjustment to ca. 2, the concentrate was subjected to extraction with THF, followed by drying with magnesium sulfate. The solvent was distilled off under vacuum to yield the end product (1.34 g).

$^1$H–NMR (CDCl$_3$, δ): 2.18(6H, s), 3.14(3H, s), 5.04(2H, s), 6.9–7.5(5H, m), 7.76(2H, s)

REFERENCE EXAMPLE 20

Synthesis of Diethyl N-(N'-Carbobenxzoxy-N'-methyl-4-amino-3,5-dimethylbenzoyl)-L-glutamate The compound (1.34 g) synthesized in Reference Example 19 was added to thionyl chloride (10 ml) and dimethylformamide was further added in a catalytic amount, followed by stirring at room temperature for 3 h. Then, the reaction solution was concentrated to dryness under vacuum. The resulting solids was dissolved in dichloromethane (25 ml) and to the resulting solution, an aqueous solution (25 ml) of diethyl glutamate ester HCl (1.0 g) and potassium carbonate (1.2 g) were added; thereafter, the reaction solution was adjusted to pH of ca. 10 with potassium carbonate, followed by vigorous stirring overnight at room temperature. The dichloromethane layer was recovered by separation, washed with 1N HCl, a saturated aqueous solution of sodium hydrogen carbonate and a saturated aqueous solution of NaCl, and dried with sodium sulfate. The solvent was distilled off under vacuum to yield the end product (2.14 g).

¹H–NMR (CDCl₃, δ): 1.23(3H, t, J = 7 Hz), 1.31(3H, t, J = 7 Hz),
2.1–2.7(4H, m), 2.17(6H, s), 3.13(3H, s),
4.13(2H, q, J = 7 Hz), 4.25(2H, q, J = 7 Hz),
4.73(1H, m), 5.07(2H, s), 6.94(1H, d, J = 8 Hz),
7.1–7.5(5H, m), 7.51(2H, s)

REFERENCE EXAMPLE 21

Synthesis of Diethyl N-[N'-Methyl-(4-amino-3,5-dimethylbenzoyl)-L-glutamate

A solution of 30% hydrogen bromide/acetic acid (24 ml) was added to an anisole solution (2.4 ml) of the compound (2.4 g) synthesized in Reference Example 20 and the mixture was stirred at room temperature for 3 h. Then, ca. 200 ml of ether was added to the reaction solution, whereupon a reddish brown oil was precipitated. The greater part of the ether layer was removed and the oil was suspended in chloroform. The suspension was washed with a saturated aqueous solution of sodium hydrogen carbonate and the organic layer was recovered by separation. The separated organic layer was dried with sodium sulfate and the solvent was distilled off under vacuum to yield the end product (1.2 g).

¹H–NMR (CDCl₃, δ): 1.21(3H, t, J = 7 Hz), 1.29(3H, t, J = 7 Hz),
2.0–2.8(4H, m), 2.29(6H, s), 2.87(3H, s),
3.11(1H, s), 4.11(2H, q, J = 7 Hz),
4.23(2H, q, J = 7 Hz), 4.83(1H, m),
6.83(1H, d, J = 8 Hz), 7.43(2H, s)

EXAMPLE 10

Synthesis of Diethyl N-{4-[N'-(2,4-Diamino-6-pteridinyl)methyl-N'-methylamino]-3,5-dimethylbenzoyl}-L-glutamate The compound (1.2 g) synthesized in Reference Example 21 and an isopropanol adduct of 6-bromomethyl-2,4-diaminopteridine hydrobromide (1.0 g) were suspended in dimethylacetamide (20 ml) and the suspension was stirred at 60° C. for 12 h. To the cooled reaction solution, water was added and the mixture was stirred, followed by extraction with chloroform. The chloroform layer was dried with sodium sulfate and the solvent was distilled off under vacuum. The resulting residue was subjected to silicagel column chromatography and elution was conducted with a solvent system of chloroform and methanol (99:1–95:5), yielding the end compound (0.64 g).

¹H–NMR (CDCl₃, +CD₃OD, δ): 1.25(3H, t, J = 7 Hz), 1.32(3H, t, J = 7 Hz),
2.0–2.7(4H, m), 2.42(6H, s),
2.82(3H, s), 4.18(2H, q, J = 7 Hz),
4.28(2H, q, J = 7 Hz) , 4.42(2H, s)
4.78(1H, m), 7.53(2H, s), 8.89(1H, s,)

EXAMPLE 11

Synthesis of N-{4-[N'-(2,4-Diamino-6-pteridinyl)methyl-N'-methylamino]-3,5-dimethylbenzoyl}-L-glutamic Acid (Compound 5)

The compound (0.59 g) synthesized in Example 10 was dissolved in a solvent system of ethanol (40 ml) and THF (20 ml); after adding an aqueous solution of 1N NaOH (3.5 ml), the mixture was stirred overnight at room temperature. The solvent was distilled off under vacuum and the resulting yellow solids was dissolved in water (20 ml) and the solution was adjusted to pH of 3.7 with 1N HCl under cooling with ice. The separating precipitate was recovered by filtration, washed successively with water and acetone, and vacuum-dried to yield the end product (0.47 g).

¹H–NMR (DMSO-d₆, δ): 1.8–2.2(2H, m), 2.3–2.5(2H, m),
2.34(6H, s), 2.73(3H, s), 4.3–4.5(1H, m),
4.36(2H, s), 6.66(2H, s), 7.55(2H, s)
8.40(1H, d, J = 6 Hz), 8.74(1H, s)

REFERENCE EXAMPLE 22

Synthesis of 4-Methylamino-3-trifluoromethylbenzoic Acid 4-amino-3-trifluoromethylbenzoic acid (3.6 g) was suspended in trifluoroacetic anhydride (90 ml) and the suspension was stirred overnight. The solvent was distilled off under vacuum and the resulting residue was dissolved in acetone (30 ml). Methyl iodide (9.9 g) was added to the solution and the mixture was heated to 45° C.; with vigorous stirring, a potassium hydroxide powder (6.8 g) was added slowly, followed by further stirring for 1 h at 45° C. Then, the solvent was distilled off under vacuum and the resulting residue was dissolved in water (50 ml). The solution was heated under reflux for 2 h. The reaction solution was then adjusted to pH of 3.5 with 1N HCl under cooling with ice. The white precipitate was recovered by filtration and washed with a small amount of water and vacuum-dried to yield the end product (2.2 g).

¹H–NMR (CDCl₃: CD₃OD = 1:1, δ): 2.95(3H, s), 6.74(1H, d, J = 9.0 Hz), 7.96–8.12(2H, m)

REFERENCE EXAMPLE 23

Synthesis of Methyl 4-Methylamino-3-trifluoromethylbenzoate

Hydrochloric acid gas was blown, under cooling with ice, into a methanol solution (25 ml) of the compound (2.2 g) synthesized in Reference Example 22 and stirring was continued at room temperature for 4 h. The solvent was distilled off under vacuum and the resulting residue was dissolved in ethyl acetate. The solution was washed with a saturated aqueous solution of sodium hydrogen carbonate and dried with anhydrous magnesium sulfate, followed by distilling off the solvent under vacuum. The resulting residue was subjected to silica gel column chromatography and elution was conducted with a solvent system of ethyl acetate and n-hexane (1:3), yielding the end product (1.3 g).

¹H–NMR (CDCl₃, δ): 2.91(3H, s), 3.83(3H, s), 4.63(1H, bs),
6.65(1H, d, J = 9.0 Hz), 7.92–8.99(2H, m)

REFERENCE EXAMPLE 24

Synthesis of 4-[N-(2,4-Diamino-6-pteridinyl)methyl-N-methyl]amino-3-trifluoromethylbenzoic Acid Sodium hydride (0.26 g) was added, under cooling with ice in a nitrogen atmosphere, to a hexamethylphosphoric triamide solution (20 ml) of the compound (1.3 g) synthesized in Reference Example 23, and the mixture was stirred for 30 min. A ⅓ isopropanol adduct of 6-bromomethyl-2,4-diaminopteridine hydrobromide (2.8 g) was added to the reaction solution and the mixture was stirred for 30 min, followed by further stirring at 70° C. for 6 h and at room temperature for 2 days. The reaction solution was poured into dilute HCl and neutralized with a saturated aqueous solution of sodium hydrogen carbonate; the resulting brown precipitate was recovered by filtration. The recovered precipitate was vacuum dried, suspended in a solvent system of chloroform and methanol (1:1) and heated under reflux for 1 h. The insoluble matter was filtered off and the filtrate was concentrated to dryness under vacuum. The resulting residue was dissolved in methanol (50 ml) and, following addition of an aqueous solution of 1N NaOH (20 ml), the mixture was stirred at 60° C. for 1 h. Methanol was distilled off under vacuum and the insoluble matter was recovered by filtration. Under cooling with ice, 1N HCl was added for pH adjustment to 4. The orange precipitate was recovered by filtration, vacuum dried and subjected to silica gel column chromatography. Elution was conducted first using ethyl acetate as a solvent, then using a solvent system of chloroform, methanol and 28% aqueous ammonia (5:4:1). The desired fractions were concentrated to dryness under vacuum and the resulting residue was dissolved in water. Following pH adjustment to 4 with 1N HCl under cooling with ice, the resulting yellow precipitate was recovered by filtration and vacuum dried to yield the end product (102 mg).

$^1$H–NMR (DMSO-d$_6$: CDCl$_3$= 7:1, δ): 2.79(3H, s), 4.42(2H, s), 7.61(1H, d, J = 8.3 Hz), 8.11–8.17(2H, m), 8.69(1H, s)

EXAMPLE 12

Synthesis of N-{4-[N'-(2,4-Diamino-6-pteridinyl)methyl-N'-methyl]amino-3-trifluoromethylbenzoyl}-L-2-aminoadipic Acid ( Synthesis of L-2-{4-[N'-(2,4-Diamino-6-pteridinyl)methyl-N'-methyl]amino-3-trifluoromethylbenzoyl}aminoadipic Acid)

Hydroxybenzotriazole (36 mg) and dicyclohexylcarbodiimide (55 mg) were added, under cooling with ice in a nitrogen atmosphere, to a hexamethylphosphoric triamide solution (2 ml) of the compound (88 mg) synthesized in Reference Example 24, and the mixture was stirred for 30 min. Subsequently, dimethyl L-2-aminoadipate ester HCl (63 mg) and N-methylmorpholine (34 mg) were added and the mixture was slowly reverted to room temperature, followed by stirring for 2 days. The reaction solution was subjected to silica gel column chromatography and purified by elution first using chloroform as a solvent, then using a solvent system of chloroform and methanol (19:1). The desired fractions were concentrated to dryness under vacuum and dissolved in methanol (2 ml). An Aqueous solution of 1N NaOH (0.4 ml) was added under cooling with ice in a nitrogen atmosphere and the mixture was stirred for 5 h. The solvent was distilled off under vacuum and the resulting residue was dissolved in water. The insoluble matter was filtered off and the filtrate was adjusted to pH of 3.5 with 1N HCl. The resulting yellow precipitate was recovered by filtration, washed with a small amount of water and vacuum dried. The crude product was subjected to preparative thin-layer chromatography (on silica gel) and separation was effected by elution with a solvent system of chloroform, methanol and 28% aqueous ammonia (5:4:1). The effluent was concentrated to dryness under vacuum and dissolved in an aqueous solution of sodium hydrogen carbonate. After filtering off the insoluble matter, 1N HCl was added for pH adjustment to 3.5. The resulting pale yellow precipitate was recovered by filtration and vacuum dried to yield the end product (18 mg).

$^1$H-NMR (DMSO-d$_6$:CDCl$_3$=7:1, δ): 1.53–1.93(4H, m), 2.25(2H, t, J=7.3Hz), 2.75(3H, s), 4.34–4.45(3H, m), 6.91(2H, bs), 7.63–7.67(2H, m), 7.95(1H, bs), 8.16(1H, d, J=8.3Hz), 8.22(1H, s), 8.72(1H, s), 8.79(1H, d, J=7.8Hz)

REFERENCE EXAMPLE 25

Synthesis of 1-Acetyl-7-methylindoline

A solution of 7-methylindoline (10.2 g) in acetic anhydride (25 ml) was refluxed for 30 min. After cooling, the reaction solution was poured into ice water (250 ml) and the resulting crystal was filtered by means of suction, heated and vacuum dried to yield the end product (11.7 g).

$^1$H-NMR (CDCl$_3$, δ): 2.24(3H, s), 2.25(3H, s), 2.99(2H, t, J=7Hz), 4.06(2H, t, J=7Hz), 7.01(2H, s)

REFERENCE EXAMPLE 26

Synthesis of 5-Bromo-1-acetyl-7-methylindoline

Bromine (3.1 ml) was added dropwise at room temperature to an acetic acid (70 ml) solution of the compound (11.5 g) synthesized in Reference Example 25, and the mixture was stirred for 1 h. The reaction solution was poured into ice water (600 ml) and discolored by addition of Na$_2$S$_2$O$_3$. The deposit was filtered by means of suction, dissolved in hot methanol and subjected to recrystallization, yielding the end product (10.8 g).

$^1$H-NMR (CDCl$_3$, δ): 2.24(6H, s), 2.98(2H, t, J=7Hz), 4.06(2H, t, J=7Hz), 7.14(2H, s)

REFERENCE EXAMPLE 27

Synthesis of 5-Cyano-1-acetyl-7-methylindoline

The compound (10.8 g) synthesized in Reference Example 26 and copper cyanide (5.5 g) were suspended in N-methylpyrrolidinone (50 ml) and the suspension was heated in a nitrogen atmosphere at ca. 200° C. for 4 h. After cooling, the reaction solution was poured into cooled aqueous ammonia (100 ml) and the deposit was filtered by means of suction. The deposit was washed with aqueous ammonia until the blue color disappeared and, thereafter, it was dissolved in hot chloroform (50 ml). After filtration by means of suction, the filtrate was washed with water and an aqueous solution of 1N NaOH, dried with magnesium sulfate and concentrated to give the crude product. The crude product was recrystallized with acetonitrile to yield the end product (4.9 g).

| | |
|---|---|
| $^1$H-NMR (CDCl$_3$, δ): | 2.24(3H, s), 2.27(3H, s), 3.05(2H, t, J=7Hz), 4.08(2H, t, J=7Hz), 7.30(2H, s) |

REFERENCE EXAMPLE 28

Synthesis of 7-Methylindoline-5-carboxylic Acid

A mixture of the compound (4.9 g) synthesized in Reference Example 27 and conc. HCl (60 ml) was refluxed for 3 h. After cooling, the mixture was poured into ice water (200 ml) and the pH was adjusted to higher than 12 with an aqueous solution of sodium hydroxide, followed by filtration by means of suction. The filtrate was adjusted to pH of ca. 4 with HCl under cooling with ice. The deposit was recovered by filtration, washed, heated and vacuum dried to yield the end product (3.4 g).

| | |
|---|---|
| $^1$H-NMR (DMSO-d$_6$, δ): | 2.05(3H, s), 2.96(2H, t, J=8Hz), 3.54(2H, t, J=8Hz), 7.42(2H, s), 11.83(1H, br s) |

REFERENCE EXAMPLE 29

Synthesis of N-Benzyloxycarbonyl-7-methylindoline-5-carboxylic Acid

The compound (3.3 g) synthesized in Reference Example 28 was added to an aqueous solution of sodium hydroxide (0.84 g) in a nitrogen atmosphere. Following the addition of ether (60 ml), the mixture was cooled with ice. Then, an aqueous solution (15 ml) of sodium hydroxide (3.3 g) and an ether solution of benzyloxycarbonyl chloride (6.8 ml) were added dropwise simultaneously and the mixture was stirred at room temperature for 4 h. The ether layer was separated and the aqueous layer was washed with ether, followed by pH adjustment to 1–2 with 3N HCl under cooling with ice. The separating crystal was filtered by means of suction, washed with water and dried by heating to yield the end product (5.3 g).

| | |
|---|---|
| $^1$H-NMR (DMSO-d$_6$, δ): | 2.22(3H, s), 3.02(2H, t, J=7Hz), 4.10(2H, t, J=7Hz), 5.16(2H, s), 7.32(5H, s), 7.55(2H, s) |

REFERENCE EXAMPLE 30

Synthesis of Dimethyl N-(1-benzyloxycarbonyl-7-methylindoline-5-carbonyl)-L-α-aminoadipate Thionyl chloride (15 ml) was suspended in the compound (2.6 g) synthesized in Reference Example 29. To the suspension, a catalytic amount of dimethylformamide was added and the mixture was stirred at room temperature for 2 h. Then, the reaction solution was concentrated to dryness under vacuum. The resulting solids was dissolved in dichloromethane (50 ml); an aqueous solution (50 ml) of dimethyl L-α-aminoadipate HCl (2.4 g) and potassium carbonate (2.3 g) were added to the solution; the pH of the reaction solution was adjusted to ca. 10 with potassium carbonate, followed by vigorous stirring overnight at room temperature. The dichloromethane layer was recovered by separation, washed successively with 1N HCl, a saturated solution of sodium hydrogen carbonate and a saturated aqueous solution of sodium chloride, and dried with sodium sulfate. The solvent was distilled off under vacuum to yield the end product (4.2 g).

| | |
|---|---|
| $^1$H-NMR (CDCl$_3$, δ): | 1.5–2.1(4H, m), 2.2–2.6(2H, m), 2.29(3H, s), 3.00(2H, t, J=7Hz), 3.64(3H, s), 3.76(3H, s), 4.14(2H, t, J=7Hz), 4.5–5.0(1H, m), 5.18(2H, s), 6.67(1H, d, J=8Hz), 7.32(5H, s), 7.44(2H, s) |

REFERENCE EXAMPLE 31

Synthesis of Dimethyl N-(7-Methylindoline-5-carbonyl)-L-α-aminoadipate

A solution of 30% hydrogen bromide/acetic acid (42 ml) was added to an anisole (4.2 ml) solution of the compound (4.2 g) synthesized in Reference Example 30 and the mixture was stirred at room temperature for 4 h. Then, ca. 400 ml of ether was added to the reaction solution, whereupon a reddish brown oil was precipitated. The greater part of the ether layer was removed and the oil was suspended in chloroform; the suspension was washed with a saturated solution of a sodium hydrogen carbonate and the end product was extracted with chloroform. The chloroform layer was dried with sodium sulfate and the solvent was distilled off under vacuum to yield the end product (2.6 g).

| | |
|---|---|
| $^1$H-NMR (CD$_3$OD, δ): | 1.5–2.1(4H, m), 2.15(3H, s), 2.38(2H, t, J=7Hz), 3.05(2H, t, J=7Hz), 3.60(2H, t, J=7Hz), 3.66(3H, s), 3.73(3H, s), 4.3–4.8(1H, m), 7.46(2H, s) |

EXAMPLE 13

Synthesis of Dimethyl N-{1-[(2,4-Diamino-6-pteridinyl)methyl]-7-methylindoline-5-carbonyl}-L-α-aminoadipate The compound (2.6 g) synthesized in Reference Example 31 and in isopropanol adduct of 6-bromomethyl-2,4-diaminopteridine hydrobromide (3.0 g) were suspended in dimethylacetamide (40 ml) and the suspension was stirred at 60° C. for 12 h. After cooling the reaction solution, water was added and the mixture was stirred; the pH of the mixture was adjusted to ca. 8 with sodium hydrogen carbonate and the insoluble matter was recovered by filtration. The chloroform layers were combined and dried with sodium sulfate; the solvent was distilled off under vacuum and the resulting residue was subjected to silica gel column chromatography, followed by elution with a solvent system of chloroform and methanol (99:1–95:5) to yield the end product (2.6 g).

¹H-NMR (CDCl₃ + CD₃OD, δ): 1.5–2.2(4H, m), 2.3–2.7(2H, m), 2.40(3H, s), 2.8–3.9(4H, m), 3.69(3H, s), 3.78(3H, s), 4.6–5.1(1H, m), 4.77(2H, s), 7.46(2H, s), 8.75(1H, s)

EXAMPLE 14

Synthesis of N-{1-[(2,4-Diamino-6-pteridinyl)methyl]-7-methylindoline-5-carbonyl}-L-α-aminoadipic Acid The compound (2.6 g) synthesized in Example 13 was dissolved in a solvent system of ethanol (400 ml) and tetrahydrofuran (500 ml); after addition of an aqueous solution of 1N NaOH (15 ml), the mixture was stirred overnight at room temperature. The solvent was distilled off under vacuum and the resulting yellow solids was dissolved in water (50 ml), followed by treatment with activated carbon and filtration through Celite. The filtrate was adjusted to pH of 2 with 1N HCl under cooling with ice and the separating precipitate was recovered by filtration. Following washing with water and acetone, the precipitate was vacuum dried to yield the end product (1.4 g).

¹H-NMR (DMSO-d₆, δ): 1.4–2.0(4H, m), 2.23(2H, t, J=7Hz), 2.34(3H, s), 2.97(2H, t, J=8Hz), 3.56(2H, t, J=8Hz), 4.32(1H, m), 4.72(2H, s), 6.87(2H, s), 7.44(1H, s), 7.49(1H, s), 8.14(1H, d, J=8Hz), 8.72(1H, s)

EXAMPLE 15

Synthesis of N-{1-[(2,4-Diamino-6-pteridinyl)methyl]indole-5-carbonyl}-L-α-aminoadipic Acid (Process 1)
An aqueous saturated sodium hydrogen carbonate solution (1.0 ml) containing potassium nitrodisulfonate (Fremy's salt) (51.2 mg) was added dropwise, under cooling with ice, to an aqueous saturated sodium hydrogen carbonate solution (1.0 ml) of N-{1-[(2,4-diamino-6-pteridinyl)methyl]indoline-5-carbonyl-}-L-α-aminoadipic acid (11.0 mg) and the mixture was stirred at room temperature for 5 h. Subsequently, an aqueous saturated sodium hydrogen carbonate solution (1.0 ml) was added to the reaction solution and the mixture was subjected to high-performance liquid chromatography. The column was of YMC Pack A-322 ODS type and the elution solvent was a 25:75 mixture of methanol and 0.1M ammonium formate buffered solution (pH, 4.5). The end product (3.9 mg) was recovered by separation under the following conditions: flow rate, 2.5 ml/min; column temperature, RT; detection wavelength, 303 nm; injection volume, 200 µl.

¹H-NMR (DMSO-d₆, δ): 1.58(2H, m), 1.74(1H, m), 1.83(1H, m), 2.21(2H, t, J=7.8Hz), 4.19(1H, m), 5.57(2H, s), 6.62(1H, d), 7.6–7.8(3H, m), 8.12(1H, s), 8.17(1H, d, J=6.0Hz), 8.57(1H, s)

(Process 2)
Dichlorodicyanobenzoquinone (18 mg) was added to a dioxane suspension (20 ml) of N-{1-[(2,4-diamino-6-pteridinyl)methyl]indoline-5-carbonyl}-L-α-aminoadipic acid (20 mg) and the mixture was stirred at 80° C. for 3 h. The solvent was distilled off under vacuum and an aqueous solution of saturated sodium hydrogen carbonate (5.0 ml) was added to the residue. The mixture was subjected to high-performance liquid chromatography under the same conditions as in Process 1, thereby yielding the end produce (7.7 mg), while was recovered by separation.

(Process 3)
An acetic acid solution (10 ml) of N-{1-[(2,4-diamino-6-pteridinyl)methyl]indoline-5-carbonyl}-L-α-aminoadipic acid (20 mg) was added dropwise to an acetic acid solution (10 ml) of manganese (III) acetate (1.5 mg) and the mixture was stirred at 80° C. for 1 h. Acetic acid was distilled off under vacuum and an aqueous solution of saturated sodium hydrogen carbonate (7.0 ml) was added to the residue. Then, the mixture was subjected to high-performance liquid chromatography under the same conditions as in Process 1, yielding the end product (0.8 mg), which was recovered by separation.

EXAMPLE 16

Synthesis of N-{1-[(2,4-Diamino-6-pteridinyl)methyl]indole-5-carbonyl}-L-homocysteic Acid Ammonium Salt The procedure of Process 1 in Example 15 was repeated, except that N-{1-[(2,4-diamino-6-pteridinyl)methyl]indoline-5-carbonyl)-L-α-aminoadipic acid was replaced by N-{1-[82,4-diamino-6-pteridinyl)methyl]indoline-5-carbonyl}-L-homocysteic acid ammonium salt (10.0 mg). As a result, the end product was yielded (4.4 mg).

¹H—NMR (DMSO-d₆, δ): 2.0–2.2(2H, m), 2.56(2H, t, J=7.3Hz), 4.35(1H, m), 5.56(2H, s), 6.61(1H, m), 7.6–7.8(3H, m), 8.17(1H, s), 8.58(1H, s), 8.82(1H, m)

EXAMPLE 17

Synthesis of N-{1-[(2,4-Diamino-6-pteridinyl)methyl]indole-5-carbonyl}-L-glutamic Acid (Compound 6)

The procedure of Process 1 in Example 15 was repeated, except that N-{1-[(2,4-diamino-6-pteridinyl)methyl]indoline-5-carbonyl}-L-aminoadipic acid was replaced by N-{1-[(2,4-diamino-6-pteridinyl)methyl]indoline-5-carbonyl}-L-glutamic acid (10.4 mg). As a result, the end product was yielded (3.1 mg).

¹H—NMR (DMSO-d₆, δ): 1.9–2.0(2H, m), 2.2–2.5(2H, m), 4.38(1H, m), 5.57(2H, s), 6.62(1H, d), 7.6–7.8(3H, m), 8.14(1H, s), 8.25(1H, m), 8.56(1H, s)

EXAMPLE 18

Synthesis of N-{1-[(2,4-Diamino-6-pteridinyl)methyl]-7-methylindole-5-carbonyl}-L-aminoadipic Acid Using N-{1-[(2,4-diamino-6-pteridinyl)methyl]-7-methyl-indoline-5-carbonyl}-L-aminoadipic acid (20 mg), the procedure of process 1 in Example 15 was repeated to yield the end product (8.4 mg).

¹H—NMR (DMSO-d₆, δ): 1.5–1.9(4H, m), 2.17(2H, m), 2.62(3H, s), 4.05(1H, m), 5.78(2H, s), 6.66(1H, d, J=3.4Hz), 7.33(1H, s), 7.59(1H, d, J=3.4Hz), 7.89(1H, m), 7.92(1H, s), 8.44(1H, s)

REFERENCE EXAMPLE 32

Synthesis of Diethyl N-(4-Nitro-3-methylbenzoyl)-L-glutamate

4-Nitro-3-methylbenzoic acid (10 g) was suspended in thionyl chloride (30 ml); thereafter, a catalytic amount of dimethylformamide was added and the mixture was refluxed for 2 h. After cooling, the reaction solution was evaporated to dryness under vacuum. The resulting solids was dissolved in dichloromethane (250 ml); to the solution, diethyl L-glutamate HCl (13.4 g), potassium carbonate (30 g) and water (250 ml) were added and the mixture was stirred vigorously at room temperature for 12 h. The reaction solution was poured into water and, following extraction with chloroform, the solution was washed with 1N HCl and dried with sodium sulfate. The solvent was distilled off under vacuum. The resulting residue was subjected to silica gel column chromatography and elution was conducted with a solvent system of chloroform and methanol (100:1) to yield the end product (10.0 g).

¹H—NMR (CDCl₃, δ): 1.2–1.4(6H, m), 2.0–2.4(2H, m), 2.4–2.6(2H, m), 2.62(3H, s), 4.14(2H, q, J=7.3Hz), 4.25(2H, q, J=7.2Hz), 4.76(1H, m), 7.44(1H, d, J=7.3Hz), 7.76(1H, m), 7.81(1H, s), 7.98(1H, d, J=8.3Hz)

REFERENCE EXAMPLE 33

Synthesis of Diethyl N-(4-Amino-3-methylbenzoyl)-L-glutamate

The compound (10.0 g) synthesized in Reference Example 32 was dissolved in acetic acid (160 ml) and a zinc powder (18 g) was added slowly to the solution under cooling with ice. After stirring at room temperature for 2 h, the mixture was filtered and the filtrate was concentrated under vacuum. The resulting concentrate was dissolved in chloroform (200 ml) and washed with a saturated aqueous solution of sodium hydrogen carbonate. The organic layer was dried with sodium sulfate and the solvent was distilled off under vacuum to yield the end product (7.8 g).

¹H—NMR (CDCl₃, δ): 1.1–1.4(6H, m), 2.0–2.4(4H, m), 2.15(3H, s), 4.0–4.3(4H, m), 4.77(1H, m), 6.62(1H, d, J=8.3Hz), 6.81(1H, d, J=7.3Hz), 7.4–7.6(2H, m)

EXAMPLE 19

Synthesis of Diethyl N-{4-[N'-(2,4-Diamino-6-pteridinyl)methylamino]-3-methyl}benzoyl-L-glutamate The compound (1.9 g) synthesized in Reference Example 33 and an isopropanol adduct of 6-bromomethyl-2,4-diaminopteridine hydrobromide (1.0 g) were suspended in dimethylacetamide (16 ml) and the mixture was stirred at 55–60° C. for 5 h. After cooling, the reaction solution was poured into a saturated aqueous solution of sodium hydrogen carbonate and subjected to extraction with a solvent system of chloroform and methanol (1:1). The organic layer was dried with sodium sulfate and the solvent was distilled off under vacuum. The resulting residue was subjected to silica gel column chromatography and elution was conducted with a solvent system of chloroform and methanol (10:1) to yield the end product (580 mg).

¹H—NMR (CDCl₃ + CD₃OD, δ): 1.2–1.4(6H, m), 2.0–2.5(4H, m), 2.30(3H, s), 4.0–4.3(4H, m), 4.67(3H, m), 6.61(1H, d, J=7.8Hz), 7.59(3H, m), 8.75(1H, s)

EXAMPLE 20

Synthesis of N-{4-[N'-(2,4-Diamino-6-pteridinyl)methylamino]-3-methyl}benzoyl-L-glutamic Acid (Compound 7)

An aqueous solution of 1N NaOH (3.5 ml) was added to an ethanol (40 ml) suspension of the compound (580 mg) synthesized in Example 19 and the mixture was stirred at 35° C. for 4 h. Following further stirring at 25° C. for 20 h, water (5 ml) was added to the reaction solution, which was then evaporated to dryness under vacuum, with care being taken so that the external temperature would not exceed 30° C. The resulting yellow solids was dissolved in water (10 ml) and the solution was adjusted to pH of 3.7 with 1N HCl, followed by standing in a refrigerator for 2 h. The deposit was precipitated by centrifuge (2000 rpm×15 min) and the supernatent was removed. The same procedure was followed five times and the resulting precipitate was dried to yield end produce (331 mg).

¹H—NMR (DMSO-d₆, δ): 1.8–2.4(4H, m), 2.25(3H, s), 4.40(1H, m), 4.60(2H, d, J=4.9Hz), 6.18(1H, m), 6.56(1H, d, J=8.3Hz), 7.56(2H, m), 8.08(1H, d, J=7.8Hz), 8.71(1H, s)

REFERENCE EXAMPLE 34

Synthesis of Dimethyl N-(3-Methyl-4-nitrobenzoyl)-L-2-aminoadipate

3-Methyl-4-nitrobenzoic acid (3.4 g) was suspended in thionyl chloride (20 ml) and, thereafter, a catalytic amount of dimethylformamide was added, followed by refluxing of the mixture for 2 h. After cooling, the reaction was evaporated to dryness under vacuum. The resulting solids was dissolved in dichloromethane (80 ml); thereafter, dimethyl L-2-aminoadipate HCl (4.2 g), potassium carbonate (10 g) and water (80 ml) were added to the solution and the mixture was stirred vigorously at room temperature for 12 h. The reaction solution was poured into water and subjected to extraction with chloroform, followed by washing with 1N HCl and drying with sodium sulfate. The solvent was distilled off under vacuum. The resulting residue was subjected to silica gel column chromatography and elution was conducted with a solvent system of chloroform and methanol (100:1) to yield the end product (6.0 g).

¹H—NMR (CDCl₃, δ): 1.6–2.4(4H, m), 2.39(2H, m), 2.62(3H, s), 3.68(3H, s), 3.80(3H, s), 4.79(1H, m), 7.13(1H, m), 7.79(2H, m), 7.98(1H, d, J=8.3Hz)

REFERENCE EXAMPLE 35

Synthesis of Dimethyl N-(4-Amino-3-methylbenzoyl)-L-2-aminoadipate

The compound (5.9 g) synthesized in Reference Example 34 was dissolved in acetic acid (100 ml) and a zinc powder (11 g) was added slowly to the solution under cooling with ice. Following stirring at room temperature for 2 h, the mixture was filtered and the filtrate was concentrated under vacuum. The resulting concentrate was dissolved in chloroform (100 ml) and washed with a saturated aqueous solution of sodium hydrogen carbonate. The organic layer was dried with sodium sulfate and the solvent was distilled off under vacuum to yield the end product (7.8 g).

¹H—NMR (CDCl₃, δ): 1.6–2.1(4H, m), 2.19(3H, s), 2.36(2H, m), 3.66(3H, s), 3.77(3H, s), 4.79(1H, m), 6.63(2H, m), 7.55(2H, m)

EXAMPLE 21

Synthesis of Dimethyl N-{4-[N'-(2,4-Diamino-6-pteridinyl)methylamino]-3-methyl}benzoyl-L-2-aminoadipate The compound (2.73 g) synthesized in Reference Example 35 and an isopropanol adduct of 6-bromomethyl-2,4-diaminopteridine hydrobromide (1.51 g) were suspended in dimethylacetamide (25 ml) and the suspension was stirred at 55–60° C. for 5 h. After cooling, the reaction solution was poured into a saturated aqueous solution of sodium hydrogen carbonate and subjected to extraction with a solvent system of chloroform and methanol (1:1). The organic layer was dried with sodium sulfate and the solvent was distilled off under vacuum. The resulting residue was subjected to silica gel column chromatography and elution was conducted with a solvent system of chloroform and methanol (10:1) to yield the end product (760 mg).

¹H—NMR (CDCl₃ + CD₃OD, δ): 1.6–2.0(4H, m), 2.29(3H, s), 2.39(2H, m), 3.68(3H, s), 3.77(3H, s), 4.65(2H, s), 4.74(1H, m), 6.62(1H, d, J=9.3Hz), 7.18(1H, d, J=7.3Hz), 7.60(2H, m), 8.77(1H, s)

EXAMPLE 22

Synthesis of N-{4-[N'-(2,4-Diamino-6-pteridinyl)methylamino]-3-methyl}benzoyl-L-2-aminoadipic Acid An aqueous solution of 1N NaOH (4.6 ml) was added to an ethanol (100 ml) suspension of the compound (760 mg) synthesized in Example 21, and the mixture was stirred at 35° C. for 4 h. Following further stirring at 25° C. for 20 h, water (10 ml) was added to the reaction solution and the mixture was evaporated to dryness under vacuum, with care being taken so that the external temperature would not exceed 30° C. The resulting yellow solids was dissolved in water (20 ml) and the solution was adjusted to pH of 3.7 with 1N HCl, followed by standing in a refrigerator for 2 h. The deposit was precipitated by centrifuge (2000 rpm×15 min) and the supernatant was removed. The same procedure was followed five times and the resulting precipitate was dried to yield the end product (400 mg).

¹H—NMR (DMSO-d₆, δ): 1.5–1.9(4H, m), 2.24(5H, m), 4.34(1H, m), 4.58(2H, m), 6.21(1H, m), 6.56(1H, d, J=8.8Hz), 7.59(2H, m), 8.05(1H, d, J=7.3Hz), 8.70(1H, s)

Industrial Applicability

The methotrexate derivatives of the present invention exhibit better lymphocyte proliferation inhibiting action than heretofore known compounds and, hence, they are very useful as rheumatism treating agents.

What is claimed is:

1. Compound represented by the formula (I)

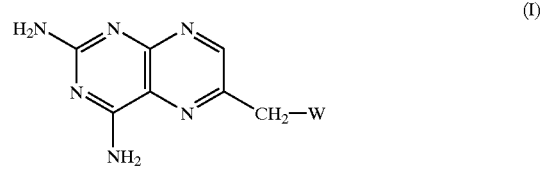

(I)

wherein W is represented by

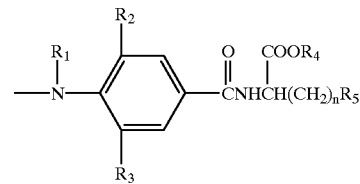

where $R_1$ is a straight chain lower alkyl group having 1–4 carbon atoms; $R_2$ is a straight chain lower alkyl group having 1–4 carbon atoms or a trifluoromethyl group; $R_3$ is a hydrogen atom, a straight chain lower alkyl group having 1–4 carbon atoms or a trifluoromethyl group; $R_4$ is a hydrogen atom or a lower alkyl group having 1–4 carbon atoms; $R_5$ is represented by the formula $COOR_6$ where $R_6$ is a hydrogen atom or a lower alkyl group having 1–4 carbon atoms, or $R_5$ is represented by the formula $SO_3H$; and n is 3; or W is represented by

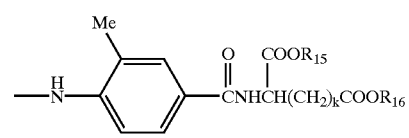

where $R_{15}$ is a lower alkyl group having 1–4 carbon atoms; $R_{16}$ is a lower alkyl group having 1–4 carbon atoms, and K is 3.

2. A compound according to claim 1 wherein W is

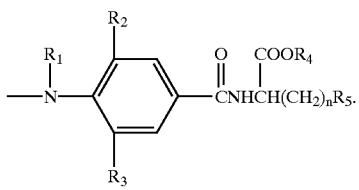

3. A compound selected from the group consisting of:

Dimethyl N-{4-[N'-(2,4-diamino-6-pteridinyl)methyl-N'-methylamino]-3-methyl}benzoyl-L-2-aminoadipate;

N-{4-[N'-(2,4-diamino-6-pteridinyl)methyl-N'-methylamino]-3-methyl}benzoyl-L-2-aminoadipic acid;

N-{4-[N'-(2,4-diamino-6-pteridinyl)methyl-N'-methylamino]-3-trifluoromethyl}benzoyl-L-2-aminoadipic acid;

Dimethyl N-{1-[2,4-diamino-6-pteridinyl)methyl]-7-methylindoline-5-carbonyl}-L-2-aminoadipate;

N-{1-[2,4-diamino-6-pteridinyl)methyl]-7-methylindoline-5-carbonyl}-L-2-aminoadipic acid;

N-{1-[2,4-diamino-6-pteridinyl)methyl]indole-5-carbonyl}-L-2-aminoadipic acid;

N-{1-[2,4-diamino-6-pteridinyl)methyl]indole-5-carbonyl}-L-homocysteic acid ammonium salt;

N-{1-[2,4-diamino-6-pteridinyl)methyl]indole-5-carbonyl}-L-glutamic acid;

N-{1-[2,4-diamino-6-pteridinyl)methyl]7-methylindole-5-carbonyl}-L-2-aminoadipic acid;

Dimethyl N-{4-[N'-(2,4-diamino-6-pteridinyl)

Dimethyl N-{4-[N'-(2,4-diamino-6-pteridinyl)methylamino]-3-methyl)benzoyl-L-2-aminoadipate; and N-{4-[N'-(2,4-diamino-6-pteridinyl)methylamino]-3-methyl)benzoyl-L-2-aminoadipic acid.

4. A compound according to claim 3, selected from the group consisting of:

Compound 3

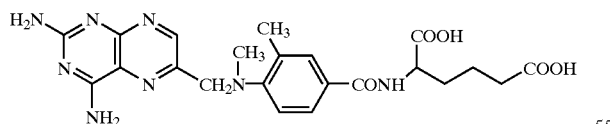

Compound 6

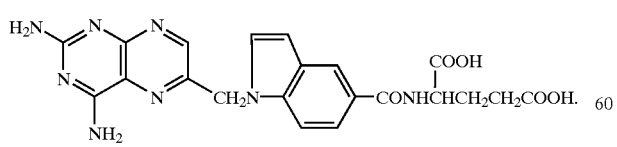

5. A method for treating rheumatism comprising administering to a patient in need of such treatment a pharmaceutically effective amount of a compound represented by formula (II)

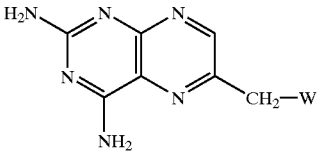

wherein W is represented by

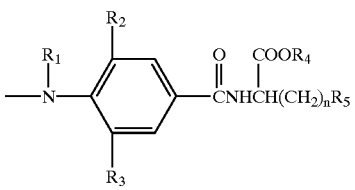

where $R_1$ is a straight chain lower alkyl group having 1–4 carbon atoms; $R_2$ is a straight chain lower alkyl group having 1–4 carbon atoms or a trifluoromethyl group; $R_3$ is having 1–4 carbon atoms or a trifluoromethyl group; $R_4$ is a hydrogen atoms or a lower alkyl group having 1–4 carbon atoms; $R_5$ is a group represented by formula $COOR_6$ where $R_5$ is a hydrogen atom or a lower alkyl group having 1–4 carbon atoms or $R_5$ is a group represented by the formula $SO_3H$; and n is an integer of 1–4, or W is represented by;

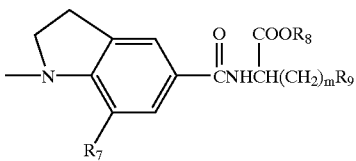

where $R_7$ is a lower alkyl group having 1–4 carbon atoms; $R_8$ is a hydrogen atom or a lower alkyl group having 1–4 carbon atoms; $R_9$ is a group represented by the formula $COOR_{10}$ where $R_{10}$ is a hydrogen atom or a lower alkyl group having 1–4 carbon atoms, or $R_6$ is a group represented by the formula $SO_3H$; and m is an integer of 1–4, or W is represented by

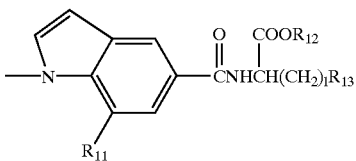

where $R_{11}$ is a hydrogen atom or a lower alkyl group having 1–4 carbon atoms; $R_{12}$ is a hydrogen atom or a lower alkyl group having 1–4 carbon atoms; $R_{13}$ is a group represented by the formula $COOR_{14}$ where $R_{14}$ is a hydrogen atoms or a lower alkyl group having 1–4 carbon atoms, or $R_{13}$ is a group represented by the formula $SO_3H$ and l is an integer of 1–4 or W is represented by

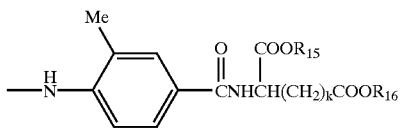

where $R_{15}$ is a hydrogen atom or a lower alkyl group having 1–4 carbon atoms; $R_{16}$ is a hydrogen atom or a lower alkyl group having 1–4 carbon atoms; and k is an integer of 2 or 3.

6. The method for treating rheumatism according to claim 5 with the proviso that, in said compound, $R_1$ is not lower alkyl when $R_2$ and $R_3$ are methyl, $R_4$ is hydrogen, n is 2 and R is COOH; and $R_1$ is not lower alkyl when $R_2$ is methyl, $R_3$ and $R_4$ are each hydrogen, n is 2 and $R_5$ is COOH.

7. The method for treating rheumatism according to claim 5, wherein said compound is selected from the group consisting of:

Diethyl N-4-[N'-(2,4-diamino-6-pteridinyl)methyl-N'methylamino]-3-methylbenzoyl-L-glutamate;

Dimethyl N-{4-[N'-(2,4-diamino-6-pteridinyl)methyl-N'-methylamino]-3-methyl}benzoyl-L-2-aminoadipate;

N-{4-[N'-(2,4-diamino-6-pteridinyl)methyl-N'-methylamino]3-methylbenzoyl}-L-glutamic acid;

Diethyl N-{4-[N'-(2,4-diamino-6-pteridinyl)methyl-N'-ethylamino]3-methylbenzoyl}-L-glutamate;

N-{4-[N'-(2,4-diamino-6-pteridinyl)methyl-N'ethylamino]-3-methylbenzoyl}-L-glutamic acid;

Diethyl N-{4-[N'-(2,4-diamino-6-pteridinyl)methyl-N'-ethylamino]3-methylbenzoyl}-L-glutamate;

N-{4-[N'-(2,4-diamino-6-pteridinyl)methyl-N'-ethylamino]-3-methyl}benzoyl-L-glutamic acid;

Dimethyl N-}4-[N'-(2,4-diamino-6-pteridinyl)methyl-N'-methylamino]3-methylbenzoyl}-L-2-aminoadipate;

N-{4-[N'-(2,4-diamino-6-pteridinyl)methyl-N'-methylamino]-3-methyl}benzoyl-L-2-aminoadipic acid;

N-(4-[N'-(2,4-diamino-6-pteridinyl)methyl-N'methylamino]-3-methylbenzoyl}-L-homocysteic acid ammonium salt;

Diethyl N-{4-[N'-(2,4-diamino-6-pteridinyl)methyl-N'-methylamino]3-ethylbenzoyl}-L-glutamate;

N-{4-[N'-(2,4-diamino-6-pteridinyl)methyl-N'-methylamino]-3-ethylbenzoyl}-L-glutamic acid;

Diethyl N-{4-[N'-(2,4-diamino-6-pteridinyl)methyl-N'-methylamino]-3,5-dimethylbenzoyl}-L-glutamate;

N-{4-[N'-(2,4-diamino-6-pteridinyl)methyl-N'-methylamino]-3,5-dimethylbenzoyl}-L-glutamic acid;

N-{4-[N'-(2,4-diamino-6-pteridinyl)methyl-N'methylamino]-3-trifluoromethylbenzoyl}-L-2-aminoadipic acid;

Dimethyl N-{4-[N'-(2,4-diamino-6-pteridinyl)methyl-7-methylindoline-5' carbonyl}-L-2-aminoadipate;

N-{1-[N'-(2,4-diamino-6-pteridinyl)methyl-7-methylindoline-5' carbonyl}-L-2-aminoadipic acid;

N-{1-[2,4-diamino-6-pteridinyl)methyl]indole-5-carbonyl}-L-aminoadipic acid;

N-{1-[2,4-diamino-6-pteridinyl)methyl]indole-5-carbonyl}-L-2-aminoadipic acid;

N-{1-[2,4-diamino-6-pteridinyl)methyl]indole-5' carbonyl}-L-homocysteic acid ammonium salt;

N-{1-[(2,4-diamino-6-pteridinyl)methyl]indole-5' carbonyl}-L-glutamic acid;

N-{1-[(2,4-diamino-6-pteridinyl)methyl-7-methylindole-5' carbonyl}-L-2-aminoadipic acid;

Diethyl N-{4-[N'-(2,4-diamino-6-pteridinyl) methylamino]3-methyl}benzoyl-L-glutamate;

Dimethyl N-{4-[N'-(2,4-diamino-6-pteridinyl) methylamino]-3-methyl}benzoyl-L-2-aminoadipate; and N-{4-[N'-(2,4-diamino-6-pteridinyl)methylamino]-3-methyl)benzoyl-L-2-aminoadipic acid.

8. A method for treating rheumatism according to claim 5 wherein said compound is selected from the group consisting of:

Compound 1
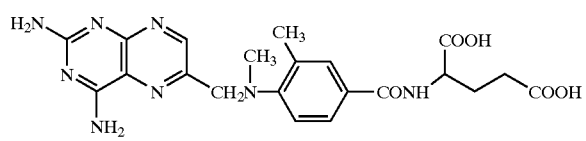

Compound 2
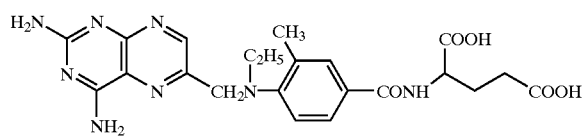

Compound 3
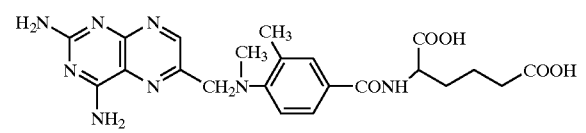

Compound 4
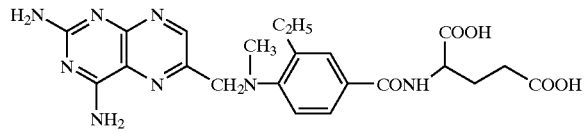

Compound 5
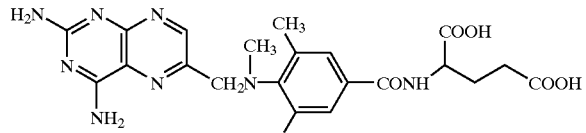

Compound 6
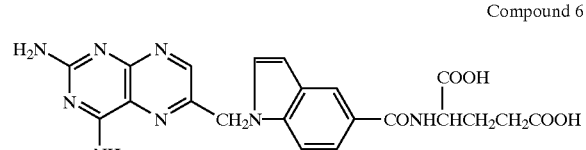

Compound 7
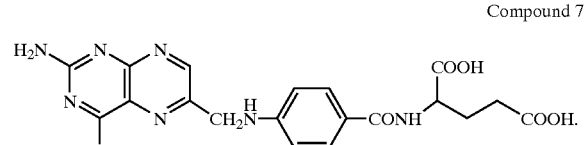

* * * * *